(12) United States Patent
Hsu et al.

(10) Patent No.: US 12,151,055 B1
(45) Date of Patent: Nov. 26, 2024

(54) DEODORIZING AIR USING AQUEOUS OZONE AS A CATALYST

(71) Applicant: Biotek Environmental Science Ltd, New Taipei (TW)

(72) Inventors: Gavin Hsu, Taipei (TW); Maxwell Hsu, New Taipei (TW); Darren Simmons, Fair Oaks Ranch, TX (US); Ivor J. J. Longo, Atlanta, TX (US); H. Brock Kolls, Alpharetta, GA (US)

(73) Assignee: Biotek Environmental Science Ltd, New Taipei (TW)

( * ) Notice: Subject to any disclaimer, the term of this patent is extended or adjusted under 35 U.S.C. 154(b) by 0 days.

(21) Appl. No.: 18/760,274

(22) Filed: Jul. 1, 2024

Related U.S. Application Data

(63) Continuation-in-part of application No. 18/646,394, filed on Apr. 25, 2024, and a continuation-in-part of application No. 18/628,680, filed on Apr. 6, 2024.

(51) Int. Cl.
| | |
|---|---|
| *A61L 9/20* | (2006.01) |
| *A61L 9/01* | (2006.01) |
| *C25B 1/02* | (2006.01) |
| *C25B 1/13* | (2006.01) |

(52) U.S. Cl.
CPC ............ *A61L 9/20* (2013.01); *A61L 9/01* (2013.01); *C25B 1/02* (2013.01); *C25B 1/13* (2013.01); *A61L 2209/212* (2013.01)

(58) Field of Classification Search
CPC ........ A61L 9/01; A61L 9/20; A61L 2209/212; C25B 1/02; C25B 1/13
See application file for complete search history.

(56) References Cited

FOREIGN PATENT DOCUMENTS

CN 106853331 A * 6/2017 ............. B01D 53/78

OTHER PUBLICATIONS

Translation of CN-106853331-A (Year: 2017).*

* cited by examiner

*Primary Examiner* — Sean E Conley
(74) *Attorney, Agent, or Firm* — H. Brock Kolls

(57) ABSTRACT

The present invention relates to a system and method of deodorizing air using aqueous ozone as a catalyst. Water is delivered to an electrochemical ozone generator which forms aqueous ozone gas, oxygen gas, and hydrogen gas. The first treatment stage oxidizes airflow extracted from a surrounding environment by combining the airflow with the aqueous ozone gas, oxygen, and hydrogen forming an oxidized airflow. A second stage deodorizes the oxidized airflow to form a deodorized airflow with hydroxide molecules that are created by combining the oxidized airflow with ultraviolet light, titanium oxide particles, and sintered columnar manganese dioxide particles. Residual aqueous ozone gas is converted to oxygen by interaction with the titanium oxide particles and the sintered columnar manganese dioxide particles. The deodorized airflow is vented back to the surrounding environment with ozone gas at or below the human-safe permissible level.

25 Claims, 14 Drawing Sheets

100

102

202

100/102

DEODORIZING AIR USING AQUEOUS OZONE AS A CATALYST

CROSS-REFERENCE TO RELATED APPLICATIONS

This application contains subject matter which is related to the subject matter of the following co-pending application. The below-listed application is hereby incorporated herein by reference in its entirety:

This U.S. non-provisional application is a continuation in part of a U.S. non-provisional application Ser. No. 18/628,680, inventor Darren Simmons et al., entitled "FOOD PREPARATION DISINFECTION TREATMENT METHODS", filed Apr. 6, 2024; which is a continuation in part of U.S. non-provisional application Ser. No. 18/428,523, inventor Darren Simmons et al., entitled "AQUEOUS OZONE DISINFECTION SYSTEM", filed Jan. 31, 2024; and This U.S. non-provisional application is a continuation in part of a U.S. non-provisional application Ser. No. 18/646,394, inventor Darren Simmons et al., entitled "AQUEOUS OZONE FLOOR DISINFECTION SYSTEM", filed Apr. 25, 2024; which is a continuation in part of U.S. non-provisional application Ser. No. 18/528,194, inventor Darren Simmons et al., entitled "AQUEOUS OZONE FLOOR DISINFECTION SYSTEM", filed Dec. 4, 2023; and a continuation in part of U.S. non-provisional application Ser. No. 18/528,162, inventor Darren Simmons et al., entitled "AQUEOUS OZONE FLOOR DISINFECTION SYSTEM", filed Dec. 4, 2023, now U.S. Pat. No. 11,975,118.

TECHNICAL FIELD OF THE INVENTION

This invention relates to a system and method of deodorizing air using aqueous ozone as a catalyst. The first treatment stage oxidizes airflow extracted from a surrounding environment, and the second stage deodorizes the oxidized airflow to form a deodorized airflow with hydroxide molecules that are created by combining the oxidized airflow with ultraviolet light, titanium oxide particles, and manganese dioxide particles. Residual humid aqueous ozone gas is reduced to a human-safe permissible level in the deodorized airflow. The deodorized airflow is vented back to the surrounding environment with the humid aqueous ozone gas at or below the human-safe permissible level.

BACKGROUND OF THE INVENTION

Before our invention air handling systems that use corona discharge ozone could typically not be used in places where people were present. Health concerns regarding breathing high concentration levels of ozone gas, as well as, breathing the more dangerous airborne nitrogen species of molecules created as a byproduct of the corona discharge process are the most commonly cited reasons.

A shortcoming is that while ozone is a superior disinfectant and deodorizer, breathing health concerns have seen the rise instead of fragrant sprays which are neither long-lasting, good for the environment, or any better for people to breathe.

The present invention addresses these and other shortcomings by providing a system and method of deodorizing air using aqueous ozone as a catalyst while preventing residual ozone from being vented into the surrounding environment, and other advantages. For these reasons and shortcomings as well as other reasons and shortcomings there is a long-felt need that gives rise to the present invention.

SUMMARY OF THE INVENTION

The shortcomings of the prior art are overcome and additional advantages are provided through the provision of a method of deodorizing air that comprises the steps of extracting a water condensate from air in a surrounding environment and delivering the water condensate to an electrochemical ozone generator to form a humid aqueous ozone gas and an oxygen gas.

The method continues by delivering, from the electrochemical ozone generator, the humid aqueous ozone gas and the oxygen gas to a first treatment stage, and oxidizing an airflow extracted from a surrounding environment by combining, in the first treatment stage, the airflow with the humid aqueous ozone gas and the oxygen gas forming an oxidized airflow.

The method continues by deodorizing the oxidized airflow to form a deodorized airflow in a second treatment stage with a plurality of hydroxide molecules that are created by combining the oxidized airflow with an ultraviolet light, a plurality of titanium oxide particles, and a plurality of manganese dioxide particles.

The method continues by reducing to a human-safe permissible level the remaining portion of the humid aqueous ozone gas in the deodorized airflow to oxygen by way of interaction with the plurality of titanium oxide particles and the plurality of manganese dioxide particles and venting the deodorized airflow back into the surrounding environment with the humid aqueous ozone gas level at or below the human-safe permissible level.

Additional shortcomings of the prior art are overcome and additional advantages are provided through the provision of a method of deodorizing air that comprises the steps of extracting a water condensate from the air in a surrounding environment and delivering the water condensate to an electrochemical ozone generator to form a humid aqueous ozone gas and an oxygen gas.

The method continues by combining the airflow with the humid aqueous ozone gas and the oxygen gas forming an oxidized airflow and deodorizing the oxidized airflow to form a deodorized airflow with a plurality of hydroxide molecules that are created by combining the oxidized airflow with a plurality of titanium oxide particles and a plurality of manganese dioxide particles.

The method continues by reducing to a human-safe permissible level the remaining portion of the humid aqueous ozone gas in the deodorized airflow to oxygen by way of interaction with the plurality of titanium oxide particles and the plurality of manganese dioxide particles, and venting the deodorized airflow back to the surrounding environment with the humid aqueous ozone gas at or below the human-safe permissible level.

Additional shortcomings of the prior art are overcome and additional advantages are provided through the provision of a method of deodorizing air that comprises the steps of extracting a water condensate from air in a surrounding environment and delivering the water condensate to an electrochemical ozone generator to form a humid aqueous ozone gas and an oxygen gas.

The method continues by combining the airflow with the humid aqueous ozone gas and the oxygen gas forming an oxidized airflow and deodorizing the oxidized airflow to form a deodorized airflow with a plurality of hydroxide molecules that are created by combining the oxidized airflow with an ultraviolet light and a plurality of titanium oxide particles.

The method continues by reducing to a human-safe permissible level the remaining portion of the humid aqueous ozone gas in the deodorized airflow to oxygen by way of interaction with the plurality of titanium oxide particles. And, venting the deodorized airflow back to the surrounding environment with the humid aqueous ozone gas at or below the human-safe permissible level.

Additional shortcomings of the prior art are overcome and additional advantages are provided through the provision of an air deodorizing system that comprises an electrochemical ozone generator that forms a humid aqueous ozone gas and an oxygen gas from a water source.

The air deodorizing system further comprises a blower that creates an airflow extracted from a surrounding environment, and a first treatment stage that creates an oxidized airflow from the airflow by combining the airflow with the humid aqueous ozone gas and the oxygen.

The air deodorizing system further comprises an ultraviolet (UV) light, a plurality of titanium oxide particles, a plurality of manganese dioxide particles, and a second treatment stage that reduces to a human-safe permissible level the remaining portion of the humid aqueous ozone gas in the deodorized airflow to oxygen by way of combining the oxidized airflow with the ultraviolet light, the plurality of titanium oxide particles, and the plurality of manganese dioxide particles to create a plurality of hydroxide molecules that operate to deodorize the oxidized airflow forming a deodorized airflow that is vented back to the surrounding environment with the humid aqueous ozone gas at or below the human-safe permissible level.

Additional shortcomings of the prior art are overcome and additional advantages are provided through the provision of an air deodorizing system that comprises a dehumidifier that makes water condensate from air a surrounding environment, and an electrochemical ozone generator that forms a humid aqueous ozone gas and an oxygen gas from the condensate water.

The air deodorizing system further comprises a blower that creates an airflow extracted from the surrounding environment, and a first treatment stage that creates an oxidized airflow from the airflow by combining the airflow with the humid aqueous ozone gas, the oxygen, and the hydrogen The air deodorizing system further comprises a plurality of titanium oxide particles, a plurality of manganese dioxide particles, and a second treatment stage that reduces to a human-safe permissible level the remaining portion of the humid aqueous ozone gas in the deodorized airflow to oxygen by way of combining the oxidized airflow with the plurality of titanium oxide particles, the plurality of manganese dioxide particles, and the humid aqueous ozone gas supplied from the electrochemical ozone generator to the second treatment stage to create a plurality of hydroxide molecules that operate to deodorize the oxidized airflow forming a deodorized airflow that is vented back to the surrounding environment with the humid aqueous ozone gas at or below the human-safe permissible level.

Additional shortcomings of the prior art are overcome and additional advantages are provided through the provision of an air deodorizing system that comprises an electrochemical ozone generator that forms a humid aqueous ozone gas and an oxygen gas from a water source, a blower that creates an airflow extracted from a surrounding environment, a first treatment stage that creates an oxidized airflow from the airflow by combining the airflow with the humid aqueous ozone gas and the oxygen, and a second treatment stage.

The air deodorizing system further comprises a plurality of titanium oxide particles and a plurality of manganese dioxide that are contained in a consumables cartridge that is inserted, in a removable manner, in the second treatment stage, and the second treatment stage reduces to a human-safe permissible level the remaining portion of the humid aqueous ozone gas in the deodorized airflow to oxygen by way of combining the oxidized airflow with the plurality of titanium oxide particles and the plurality of manganese dioxide particles to create a plurality of hydroxide molecules that operate to deodorize the oxidized airflow forming a deodorized airflow that is vented back to the surrounding environment with the humid aqueous ozone gas at or below the human-safe permissible level.

System and computer program products corresponding to the above-summarized methods are also described and claimed herein.

Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE FIGURES

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

The detailed description explains the preferred embodiments of the invention, together with advantages and features, by way of example with reference to the drawings.

DETAILED DESCRIPTION OF THE INVENTION

Figure 1:
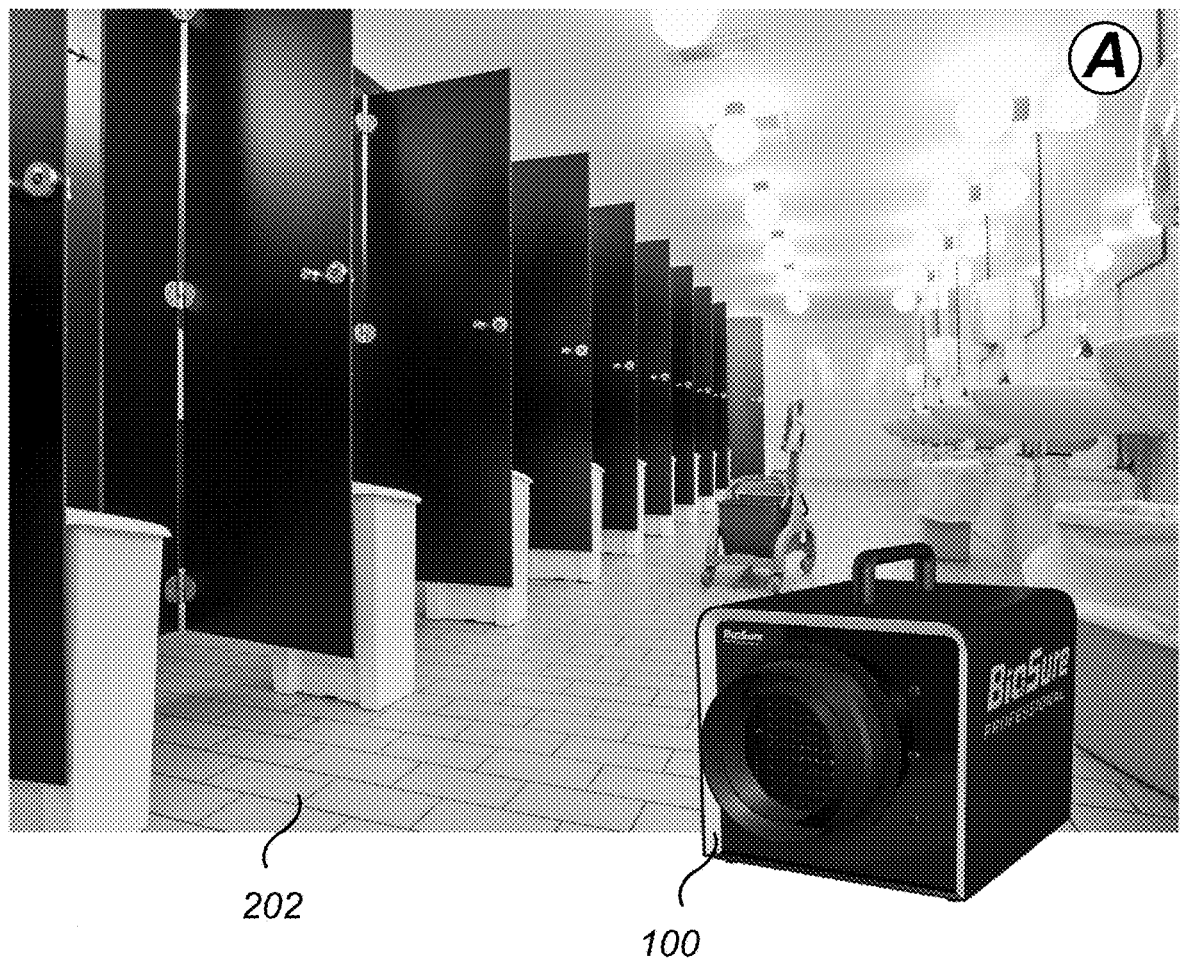
FIGS. 1-4 illustrate examples of an air deodorizing system.
Figure 1:
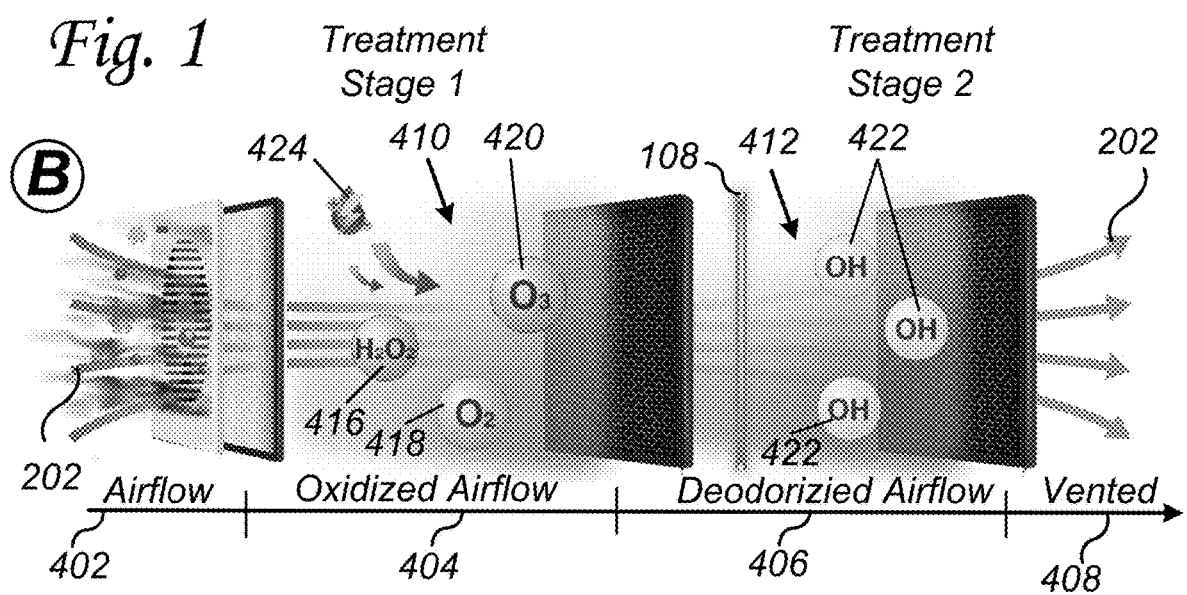

Turning now to the drawings in greater detail, it will be seen that in FIG. 1 there is illustrated one example of an air deodorizing system 100. In an exemplary embodiment in reference 'A', the present invention deodorizes the air in a surrounding area 202 such as a public bathroom, other public spaces, homes, businesses, and other types or kinds of surrounding areas 202.

An advantage, in the present invention, is that aqueous ozone is used as a catalyst in the deodorization of airflow through the air deodorizing system 100 but prior to venting the deodorized air back into the surrounding area 202 the ozone is converted to oxygen. In this regard, though aqueous ozone is used as a catalyst, ozone is not vented into the surrounding environment. As such the present invention can be used in spaces where people are present without the worry of ozone being present in the air at elevated levels which is a shortcoming of prior ozone-based systems.

In this regard, in the present invention, in FIG. 1 reference 'B', airflow 402 extracted from the surrounding environment enters a first treatment stage 410 where airflow 402 is combined with electrochemically generated ozone gas, oxygen gas, and hydrogen gas to form hydrogen peroxide $H_2O_2$ 416, oxygen $O_2$ 418, ozone $O_3$ 420, and humidity 424. The resultant is an oxidized airflow 404. The oxidized airflow 404 then enters a second treatment stage 412 where it is mixed with ultraviolet light 108, a plurality of titanium oxide particles 110, and a plurality of manganese dioxide particles 112 to create a plurality of hydroxide molecules 422 that operate to deodorize the oxidized airflow 404 forming the deodorized airflow 406. The deodorized airflow 406 is then vented 408 back to the surrounding environment 202 the ozone gas 420 which is reduced to human-safe permissible levels by conversion to oxygen during the process. The reduction to human-safe permissible levels of ozone gas in the vented 408 air allows the present invention to be used in the presence of people.

In an exemplary embodiment, the plurality of manganese dioxide particles can be a plurality of sintered columnar manganese dioxide particles or other suitable manganese dioxide.

The maximum amount of ozone gas that can be vented into the environment while still being considered safe for humans referred to as the human-safe permissible level, is determined by health and safety guidelines set by regulatory agencies such as the Occupational Safety and Health Administration (OSHA) in the United States and the World Health Organization (WHO).

The OSHA Permissible Exposure Limit (PEL) also referred to as the human-safe permissible level for disclosure purposes, sets the permissible exposure limit for ozone in the workplace at 0.1 parts per million (ppm) for an 8-hour workday and a 40-hour workweek.

The World Health Organization (WHO) Guideline Value, also referred to as the human-safe permissible level for disclosure purposes, recommends a guideline value of 0.05 ppm (100 μg/m³) for an 8-hour average.

The Environmental Protection Agency (EPA) National Ambient Air Quality Standards (NAAQS), also referred to as the human-safe permissible level for disclosure purposes, sets the primary standard for ground-level ozone at 0.070 ppm averaged over 8 hours, which is intended to protect public health, including the health of sensitive populations such as children, the elderly, and those with respiratory issues.

In an exemplary embodiment, the human-safe permissible level can be in the range of less than 0.1 parts-per-million (ppm) for an 8-hour workday and a 40-hour workweek.

Another advantage, in the present invention, is that a dehumidifier is used to create a water condensate 204 from the air. This allows the aqueous ozone generator to operate producing electrochemically generated ozone without the need for a supply of water to be provided by plumbing or human adding. In operation, the ability to self-produce water condensate from the air allows the present invention to be mounted in a location that would otherwise be difficult to plumb a water supply or have a human refill a water supply. Such locations can include aerial mount on ceilings, in recessed areas, and other hard-to-ge-to-easily types of places, as may be required and/or desired in a particular embodiment.

An advantage, in the present invention, is that aqueous ozone production happens within water and in the absence of air or oxygen gas traditionally used on corona discharge ozone production. The advantage of aqueous ozone is that it forms ozone $O_3$ molecules in large quantities on demand from the water with the help of an ion exchange material. The ozone molecules are produced in high concentration levels and well distributed throughout the water and tend not to break out of the water which makes the aqueous ozone concentration slow to dissipate with a half-life in the range of 20-30 minutes.

In contrast, corona discharge systems create ozone gas (and a bunch of human-harmful nitrogen species molecules) that then has to be dissolved or dispersed into the water at a low concentration level which easily breaks out of the water and dissipates before any real disinfection benefits can be realized. Additionally, the ozone purity level in aqueous ozone is in the range of 20% to 28%, whereas corona discharge techniques yield ozone purity in the mid-single digits to low teens with corona discharge in air having lower purity than corona discharge in oxygen.

In an exemplary embodiment, an air deodorizing system 100 can use aqueous ozone as a catalyst. The air deodorizing system can comprise an electrochemical ozone generator 516 that forms a humid aqueous ozone gas, an oxygen gas, and a hydrogen gas from a water source. Such water sources can be a plumbed or piped water source, a human-refilled water source, a water condensate from a dehumidifier 124, or other suitable water source. Additionally, tank 126 can be used to store the water source.

An advantage, in the present invention, is that by creating ozone from water (i.e. aqueous ozone), the extracted ozone gas 420 is humid 424 and the result can be referred to as humid aqueous ozone gas. The water vapor 424 associated with the humid aqueous ozone gas aids the oxidation of the airflow and subsequent deodorization of the airflow improving the performance of the air deodorizing system 100.

An advantage, in the present invention, is that by use of the electrochemical generator 516 which employs both electrolysis and an ion exchange 534 process, oxygen gas, hydrogen gas, and ozone gas can be produced and extracted, and used in the air deodorizing system and methods.

The air deodorizing system 100 can further comprise a blower 104 that creates an airflow 402 extracted from a surrounding environment 202. In this regard, a fan or blower 104 can be configured to draw airflow 402 into the air deodorizing system 100 from the surrounding environment 202.

An ultraviolet (UV) light 108 aids in the oxidizing and deodorizing of the airflows 402, 404, 406, and 408. The ultraviolet light 108 can be positioned to illuminate the interior areas of the air deodorizing system 100.

The air deodorizing system 100 can further comprise a first treatment stage 410 that creates an oxidized airflow 404 from the airflow 402 by combining the airflow 402, the humid aqueous ozone gas, the oxygen, and the hydrogen. Tube or pipe 120 can be used to deliver the humid aqueous ozone gas, the oxygen, and the hydrogen from the aqueous ozone generator 530 to the first treatment stage.

The air deodorizing system 100 can further comprise a plurality of titanium oxide particles 110, a plurality of manganese dioxide particles 112, and a second treatment stage 412.

In operation, the second treatment stage 412 creates a deodorized airflow 406 from the oxidized airflow 404 and converts the remaining portion of the humid aqueous ozone gas in the deodorized airflow 406 to oxygen by way of combining the oxidized airflow 404 with ultraviolet light 108, the plurality of titanium oxide particles 110, and the plurality of manganese dioxide particles 112 to create a plurality of hydroxide molecules that operate to deodorize the oxidized airflow 404 forming the deodorized airflow 406. The deodorized airflow 406 is then vented 408 back to the surrounding environment 202 with the humid aqueous ozone gas at or below a human-safe permissible level.

Figure 2:
Figure 2:
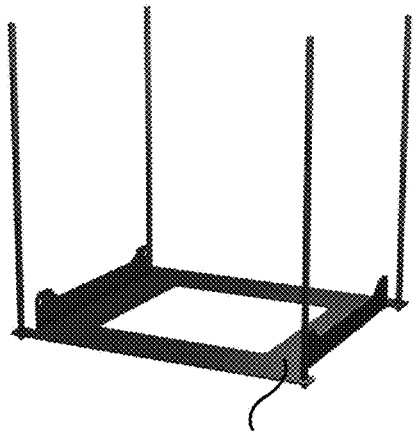
Figure 2:
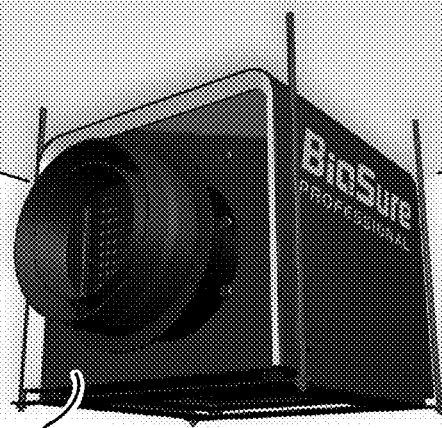

Referring to FIG. 2, there is illustrated one example of an air deodorizing system 100. In an exemplary embodiment, in reference 'A', an aerial mounting bracket 102 can be interconnected with the air deodorizing system 100. In reference 'B', The aerial mounting bracket 102 can be used to secure the air deodorizing system 100 for operation, in elevated locations, such as ceiling areas, off-the-ground locations, and other types or kinds of locations, as may be required and/or desired in a particular embodiment.

In a plurality of exemplary embodiment, the present invention can remarkably diminish the effects of airborne smells and odors, cigarette and cigar smoke, and other air quality issues in places like restrooms, casinos, hotel rooms, and numerous other places, as may be required and/or desired in a particular embodiment.

Figure 3:
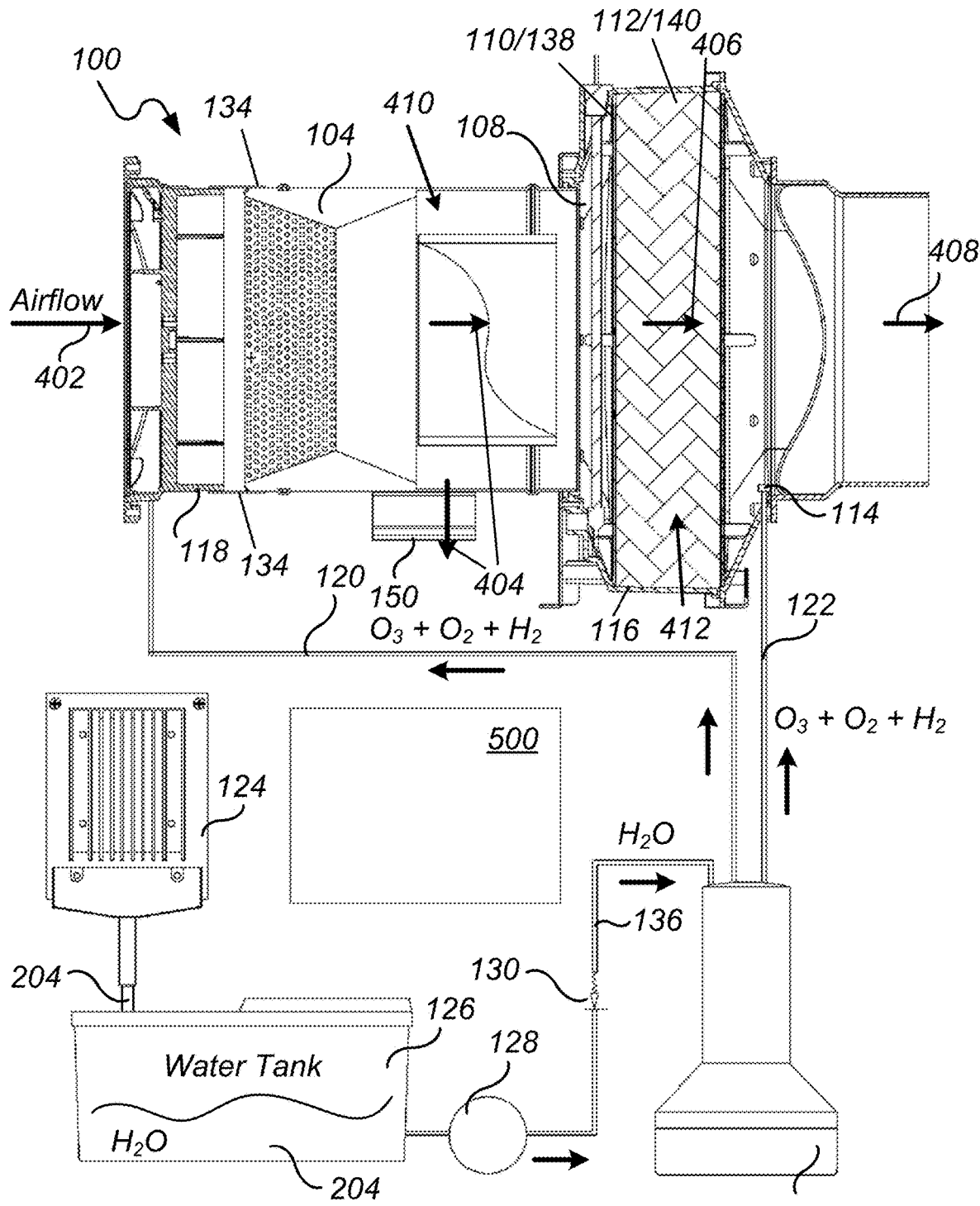

Referring to FIG. 3, there is illustrated one example of an air deodorizing system 100. In an exemplary embodiment, the air deodorizing system 100 can be packaged in a suitable enclosure 134 having an interior and an exterior. In operation, airflow 402 is drawn into the interior of housing 134 where it is deodorized and then vented from the interior of the air deodorizing system 100 back into the surrounding environment 202. In general, airflow air deodorizing system 100, is treated and then exits the air deodorizing system 100 as deodorized airflow that is at or below the human-safe permissible level of ozone so that the system can be used in the presence of people without the worry of breathing excessive ozone in the air.

The enclosure can be fabricated from metal, plastic, a combination of materials, and other suitable materials as may be required and/or desired in a particular embodiment.

In an exemplary embodiment, an air deodorizing system 100 can use aqueous ozone as a catalyst. The air deodorizing system 100 can comprise a dehumidifier 124 that makes water condensate 204 from the air. The water condensate can also be referred to as a water source. An electrochemical ozone generator 516 forms a humid aqueous ozone gas, an oxygen gas, and a hydrogen gas from the condensate water. An aqueous ozone generator 530 can comprise the electrochemical ozone generator 516 and ion exchange material 534.

In an exemplary embodiment, tank 126 receives and stores the water source/condensate 204 from the dehumidifier 124. And, pump 128 delivers the water source/condensate 204, by way of, tubing or pipe 136, or other suitable method to the electrochemical ozone generator 516. A check valve 130 can maintain a one-way flow from the water tank 126, through pump 128, and into aqueous ozone generator 530.

In an exemplary embodiment, a blower creates an airflow 402 that can be extracted from a surrounding environment 202. First treatment stage 410 then creates an oxidized airflow 404 from the airflow 402 by combining the airflow 402 with, by way of the tubing or piping connection 120, the humid aqueous ozone gas, the oxygen, and the hydrogen.

In an exemplary embodiment, the air deodorizing system 100 can further comprise an ultraviolet light 110, a plurality of titanium oxide particles 110, and a plurality of manganese dioxide particles 112.

In operation, a second treatment stage 412 creates a deodorized airflow 412 from the oxidized airflow 404 and converts the remaining portion of the humid aqueous ozone gas in the deodorized airflow 406 to oxygen by way of combining the oxidized airflow 404 with the ultraviolet light 108, the plurality of titanium oxide particles 110, the plurality of manganese dioxide particles 112, and the humid aqueous ozone gas supplied 122, by way of the tubing or piping connection 122, from the electrochemical ozone generator 516 to the second treatment stage 412 to create a plurality of hydroxide molecules that operate to deodorize the oxidized airflow 404 forming the deodorized airflow 406. Once treated the deodorized airflow is vented back to the surrounding environment with the humid aqueous ozone gas at or below a human-safe permissible level.

In operation, the turbulence of the oxidized airflow causes the plurality of titanium oxide particles 110 and the plurality of manganese dioxide particles 112 to mix and be stirred together within the second treatment stage to interact with the humid aqueous ozone gas, the oxygen gas, and the hydrogen gas to form a plurality of hydroxide molecules that operate to deodorize the oxidized airflow 404 forming the deodorized airflow 406.

In an exemplary embodiment, the second treatment stage 412 can comprise an inlet 114 which can be interconnected, by way of tubing or piping 122, with the electrochemical ozone generator for selectively receiving the humid aqueous ozone gas. In certain types of applications, a second source of the humid aqueous ozone gas can improve disinfection of the oxidized airflow 404 so that the deodorized airflow 406 is both deodorized as well as disinfected.

In an exemplary embodiment, a control system 500 can comprise a microcontroller 502, a memory 504, and a communication interface 508. The microcontroller 502 can be operationally related to memory 504 and communication interface 508. Memory 504 can be encoded with instructions that when executed by the microcontroller 502, send an operational status message, by way of a control system 500, to a remote data processing resource 702.

In this regard, operational parameters can include for example, and not a limitation correct air deodorizing system 100 operations, ozone concentration, amount of consumables remaining, service needs, operating status, runtime since last service, total run time, global position system (GPS) location, and other operational parameters, as may be required and/or desired in a particular embodiment. Such consumables can include for example, and not a limitation, the electrochemical generator 516, ion exchange material 534, the plurality of titanium oxide particles 110, the plurality of manganese dioxide particles 112, and other types and kinds of consumables.

In an exemplary embodiment, a first surface 138 associated with the second treatment stage 412 can be coated with the plurality of titanium oxide particles 110. In this regard, a large surface area can be coated with the plurality of titanium oxide particles 110 and configured so that the turbulent oxidized airflow through the air deodorizing system 100, the ultraviolet light 108, and the plurality of manganese dioxide particles 112 impinge on the first surface 138 to cause mixing of the various elements.

In an exemplary embodiment, a second surface 140 associated with the second treatment stage 412 can be coated with the plurality of manganese dioxide particles 112. In this regard, a large surface can be coated with the plurality of manganese dioxide particles 112 and configured so that the turbulent oxidized airflow through the air deodorizing system 100, the ultraviolet light 108, and the plurality of titanium oxide particles 110 impinge on the second surface 140 to cause mixing of the various elements.

An advantage, in the present invention, is that in an exemplary embodiment, a mechanical bypass 150 can be implemented to vent the oxidized airflow 404 to the surrounding environment bypassing the deodorized airflow 406 treatment. In this regard, humid aqueous ozone gas and oxygen gas can be vented within the oxidized airflow 404 into the surrounding environment. This mechanical bypass can be operated either manually by a user or automatically by the control system 500 and enables the present invention to output either an oxidized airflow 404 or a deodorized airflow 406, as may be required and/or desired in a particular embodiment.

Figure 4:
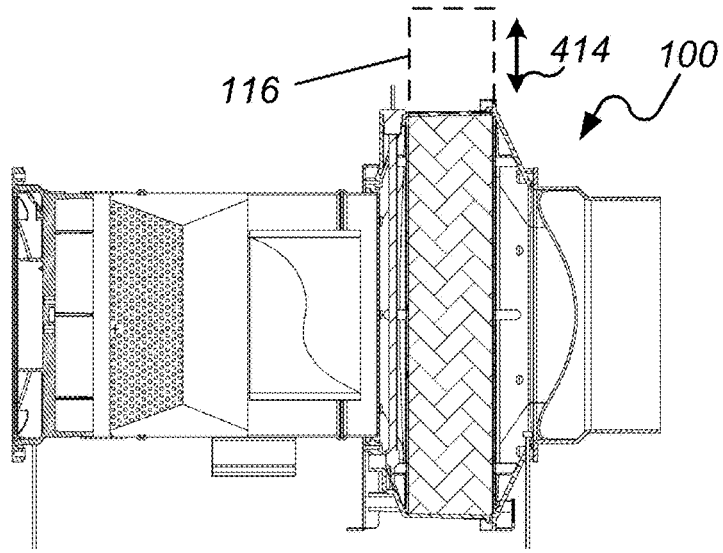

Referring to FIG. 4, there is illustrated one example of an air deodorizing system 100. In an exemplary embodiment, a consumables cartridge 116 can be inserted 414, in a removable manner, into the second treatment stage 412. The consumables cartridge can comprise a plurality of titanium oxide particles 110 and a plurality of manganese dioxide particles 112.

In an exemplary embodiment, an air deodorizing system 100 can use aqueous ozone as a catalyst. The air deodorizing system 100 can comprise an electrochemical ozone generator 516 that forms a humid aqueous ozone gas, an oxygen gas, and a hydrogen gas from a water source 204.

A blower 104 can create an airflow 402 that is extracted from a surrounding environment 202. A first treatment stage 410 can create an oxidized airflow 404 from the airflow 402 by combining the airflow 402 with the humid aqueous ozone gas, the oxygen, and the hydrogen.

The air deodorizing system 100 can further comprise an ultraviolet light 110, a plurality of titanium oxide particles, and a plurality of manganese dioxide particles.

A consumables cartridge 116 can be inserted 414, in a removable manner, in the second treatment stage 412. The consumables cartridge can comprise the plurality of titanium oxide particles 110, and the plurality of manganese dioxide particles 412.

In an exemplar embodiment, a second treatment stage 412 can be a consumables cartridge 116 that is replaceable. The second treatment stage 412 can create a deodorized airflow 406 from the oxidized airflow 404 and convert the remaining portion of the humid aqueous ozone gas in the deodorized airflow 406 to oxygen by way of combining the oxidized airflow 404 with the ultraviolet light 110, the plurality of titanium oxide particles 110, and the plurality of manganese dioxide particles 112 to create a plurality of hydroxide molecules that operate to deodorize the oxidized airflow 404 forming the deodorized airflow 406. The deodorized airflow is then vented back to the surrounding environment 202 with the humid aqueous ozone gas at or below a human-safe permissible level.

Figure 5:
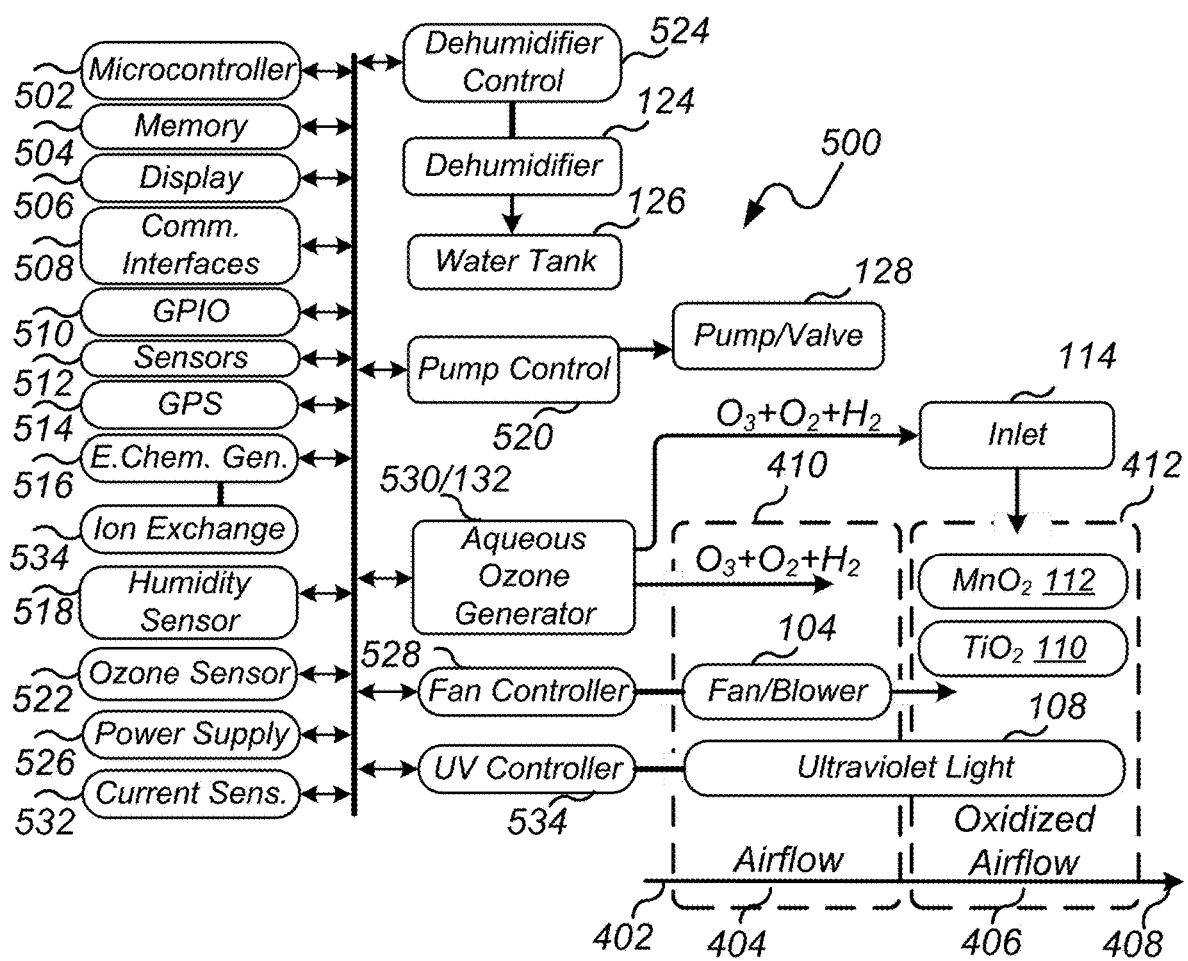
FIG. 5 illustrates one example of a control system for an air deodorizing system.

Referring to FIG. 5, there is illustrated one example of a control system 500 for the air deodorizing system 100. In an exemplary embodiment, control system 500 can be integrated into and be responsive to the action of an air deodorizing system 100. In addition, control system 500 can be a web-enabled control system.

The term "web-enabled" or "web-enabled control system" or "web-enabled control system 500" in the present invention is intended to mean an Internet-of-things device. In this regard, a device that is capable of connecting a physical device such as an air deodorizing system 100 to the digital world. Stated differently, web-enabling is equipping a device with the necessary electronics to be monitored, and controlled, and data communicate locally and remotely with other data-communicating devices. Such other data-communicating devices can be smartphones, tablets, laptops, mobile communication devices, other web-enabled devices, remote data processing resources, servers, and similar devices.

Figure 6:
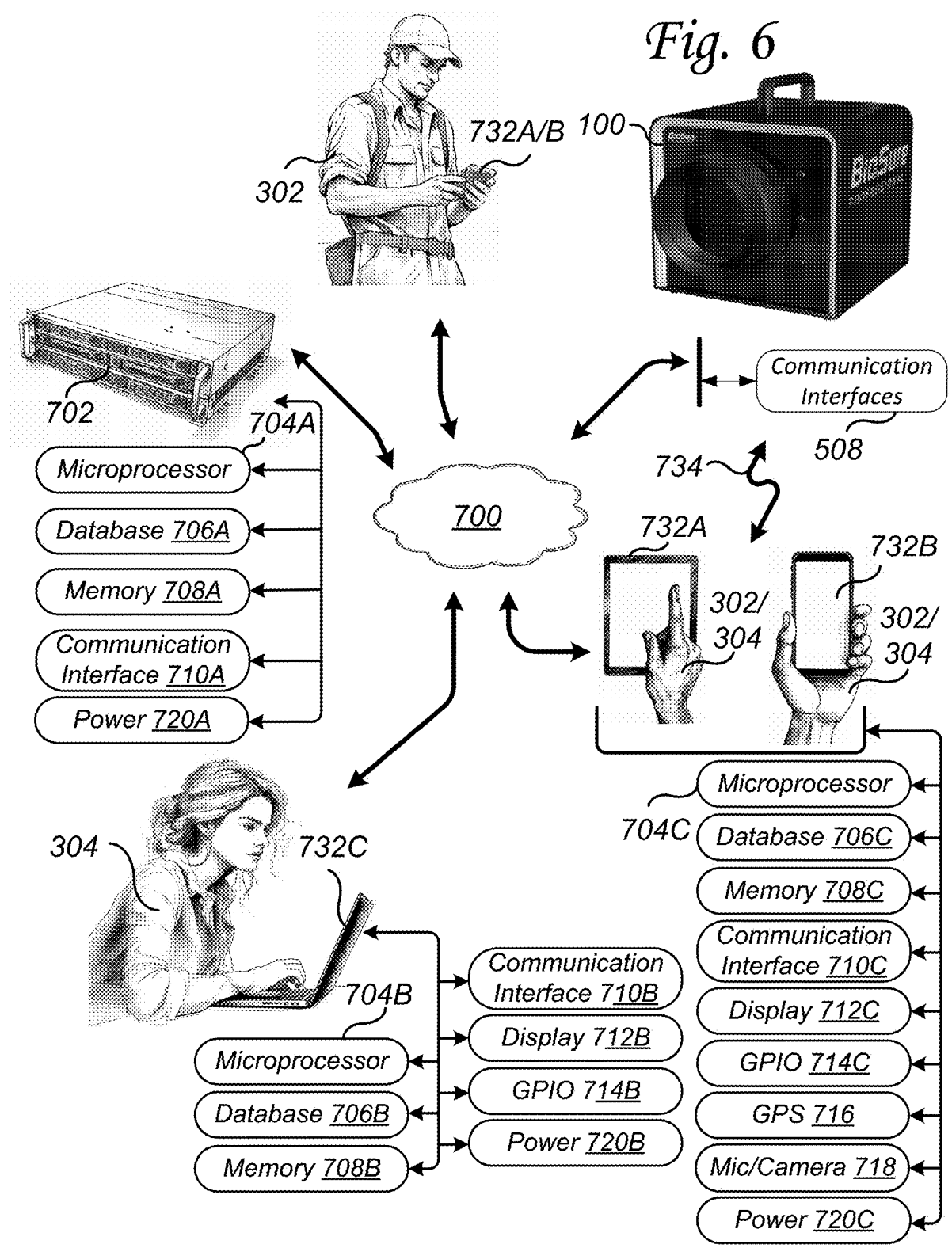
FIG. 6 illustrates one example of a system and network diagram.

In addition, and with reference to at least FIG. 6, such data communicating devices 732 can data communicate with remote data processing resources 702 and store and retrieve data from databases 706A-C, and other data processing resources, as may be required and/or desired in a particular embodiment. Laptops, smartphones, smartwatches, tablets, desktop computers, servers, mobile communication devices, and other types and kinds of data communication devices can all be data communicating devices 732 also referred to as computing devices 732.

In operation, a technician 302, an administrator 304, or other authorized people can use computing device 732 to interact with the aqueous ozone generator 530 or air deodorizing system. The aqueous ozone generator 530 can comprise the electrochemical generator 516 and ion exchange material 534.

In this regard, a technician 302 can be a person who operates, maintains, cleans, configures, repairs, and performs other functions on or with the aqueous ozone generator 530 or air deodorizing system 100. An administrator 304 can be a person who administers, provides remote service or technical support, or be other types or kinds of authorized user, as may be required and/or desired in a particular embodiment.

In operation the control system 500, by way of the communication interface 508 can data communicate with remote data processing resources 702. Such remote data processing resources 702 can be servers or other types or kinds of data processing resources. Furthermore, data communicating devices 732, remote data processing resources 702, data storage resources 706A-C, and other types and kinds of data communicating devices can data communicate over a global network 700. The Internet is a global network 700.

In an exemplary embodiment and with reference to at least FIG. 5, the air deodorizing system 100 can be equipped with a web-enabled control system 500. Such a web-enabled control system 500 can comprise a microcontroller 502 which is operationally related to a memory 504, a display 506, a plurality of communication interfaces 508, general purpose input and outputs (GPIO) 510, a plurality of sensors 512, a global position system (GPS) 514, an electrochemical generator 516, a humidity sensor 518, a pump controller 520 that is operationally related to a plurality of pumps/valves 128, a plurality of ozone sensors 522, a dehumidifier controller 524 that is operationally related to a dehumidifier 124, a power supply 526, a fan controller 528 that is operationally related to a fan/blower 104, an ultraviolet light controller 530 that is operationally related to an ultraviolet light 108, current sensor 532, and an aqueous ozone generator 530.

The microcontroller 502 can be INTEL, ZILOG, MICROCHIP, AMD, ARM, and/or other types or kinds of microcontrollers.

The memory 504 can be a combination of random access memory (RAM), read only memory (ROM), flash, hard drives, solid-state drives, USB flash drives, and/or other types and kinds of memory.

The display 506 can be a liquid crystal display (LCD), organic light emitting diode (OLED), or light emitting diode (LED), as well as have touch input capabilities and/or other types and kinds of displays and user inputs as may be required and/or desired in a particular embodiment.

The communication interface 508 can be LAN, WAN, USB, Ethernet, RS232, RS485, serial, WiFi, 802.11abgn and similar, second-generation (2G), third-generation (3G), fourth-generation (4G), or fifth-generation (5G) compatible, Bluetooth, TCP, UDP, Mesh Network, Zigbee, Pico Network, LORAN, and/or other types and kinds of communication interfaces and protocols.

In an exemplary embodiment, the communication interface 508 is operationally related to the microcontroller 502. The control system 500, by way of the communication interface 508, data communicates with the remote data processing resource 702, data communication devices 732, and other data processing resources in a local area network environment or a wide area network environment across a global network 700 in a wired or wireless manner as may be required and/or desired in a particular embodiment. The Internet is a global network 700.

The GPIO 510 can be transistor-to-transistor (TTL), complementary metal-oxide-semiconductor (CMOS), transistors, buffers, relays, pushbuttons, switches, and/or other types and kinds of GPIO circuits.

The sensors 512 and/motion sensor 518 can be passive infrared (PIR) motion sensors, infrared, thermal, Doppler radar, ultrasonic, capacitance, touch-type, optical, Hall effect, switch, fingerprint, and other types of biometric sensors, and/or other types and kinds of sensors. Additionally, sensor 512 can be ambient condition sensors such as temperature, moisture, humidity, sunlight, and/or other types and kinds of sensors.

In an exemplary embodiment, analog-type sensor determinations can be converted to digital values so that the microcontroller 502 can process the data. Alternatively, the microcontroller 502 can perform analog-to-digital conversions if equipped to perform such functions.

The electrochemical generator 516 can be an electrolysis-based device that utilizes ion exchange material 534 and other devices and processes to produce chemical compounds from water such as ozone $O_3$.

The humidity sensor 518 can be utilized to determine the surrounding environment 202 humidity level. Such humidity level can be used to determine the operating of the air deodorizing system 100. Including the time it takes to produce a suitable amount of water condensate 204, from the air, by way of the dehumidifier 124, and used for other operating conditions and/or parameters.

The pumps and/or valves 520, in addition to performing their fluid handling tasks, pumps and/or valves 520 can be actuated and/or controlled by way of a relay, metal-oxide-semiconductor field-effect transistor (MOSFET), or other types and kinds of controlling devices. In addition, other pumps and/or valves 528/532 can be integrated into the system as may be required and/or desired in a particular embodiment.

The ozone sensor 522 can be configured to monitor the ozone concentration supplied to the system or other sources of ozonated liquid, as may be required and/or desired in a particular embodiment.

The dehumidifier controller 524 is operationally related to and can be configured to monitor and operate a dehumidifier 124, as may be required and/or desired in a particular embodiment.

The power supply 526 can be AC, DC, battery, solar, and/or other types and kinds of power supplies.

The fan controller 528 is operationally related to and can be configured to monitor and operate the fan/blower 104. In this regard, turning the fan/blower on/off and/or controlling the rotational speed of the fan/blower 104, as may be required and/or desired n a particular embodiment.

The aqueous ozone generator 530 receives water as an input and uses the electrochemical generator 516 which is integrated into the aqueous ozone generator 530 to produce high concentrations of aqueous ozone molecules. Such concentrations of aqueous ozone can range from 1 ppm to 10 ppm or other desired range, as may be required and/or desired in a particular embodiment.

The current sensor 532 can be configured to measure the supplied electrical current to the electrochemical generator 516, the aqueous ozone generator 530, a combination 516/132 thereof, and/or other devices and systems, as may be required and/or desired in a particular embodiment.

The ultraviolet light (UV) controller 534 is operationally related to ultraviolet light 108 and can be configured to turn the UV light 108 on/off, vary the luminance of the UV light 108, monitor that the UV light 108 is operational, and monitor and control other features, as may be required and/or desired in a particular embodiment.

In an exemplary embodiment, a user interface for the air deodorizing system 100 can comprise at least one of the following a display 506, a display 506 with touchscreen, a communication interface 508 configured to data communicate with a remote data processing resource 702 such as a server 702 and/or a computing device 732.

The user interface for the air deodorizing system 100 can further comprise a plurality of button input capabilities by way of the GPIO 510, or other user interfaces. The user interface is operationally related to the microcontroller 502.

Referring to FIG. 6, there is illustrated one example of a system and network diagram. In an exemplary embodiment, users of the platform and network can include technicians 302, administrators 304, or other authorized persons.

Each of the users uses computing devices 732A-C to data communicate over a global communication network 700 with one or more data processing resources 702. The computing devices 732A-C can be laptop computers, desktop computers, smartphones, tablets, or other types and kinds of computing devices, as may be required and/or desired in a particular embodiment. For disclosure purposes, computing devices 732A-C can be referred to as computing devices 732. Additionally, laptop and desktop types of computing devices 732 can be referred to as computing devices 712C, computing devices 732 such as smartphones can be referred to as computing devices 732B, and computing devices 732 such as tablets can be referred to as computing devices 732A. In operation, any of the users can use any of the types of computing devices 732A-C, without limitation to the type or kind of computing device 732, as may be required and/or desired in a particular embodiment. The global communication network 700 can be the Internet.

The computing devices 732 can comprise a microprocessor 704B/704C, a database 706B/706C, memory 708B/

708C, a communication interface 710B/710C, a display 712B/712C, and a plurality of general-purpose inputs and outputs (GPIO) 714B/714C.

Additionally, mobile type of computing device 732A/732B (tablets, smartphones, and others) can comprise a global positioning system (GPS) 716, and a microphone and/or camera 718.

In general, computing devices 232 can be configured with other functions and features, as may be required and/or desired in a particular embodiment.

In an exemplary embodiment, the microprocessor 704B is operationally related to database 706B, memory 708B, communication interface 710B, display 712B, and GPIO 714B.

In an exemplary embodiment, the microprocessor 704C is operationally related to database 706C, memory 708C, communication interface 710C, display 712C, GPIO 714C, and if equipped, with GPS 716, and microphone and/or camera 718. The computing devices 732 each rely on a suitable power source 720B/720C which can include a rechargeable battery, external power supply, or other types and/or kinds of power sources.

Microprocessor 704B/704C can be INTEL, ZILOG, MICROCHIP, AMD, ARM, and/or other types or kinds of microprocessors.

Database 706B/706C can be SQL, MYSQL, MARIADB, ORACLE, MS ACCESS, network-accessible storage, flat files, a combination thereof, or other types and kinds of databases.

Memory 708B/708C can be a combination of RAM, ROM, flash, hard drives, solid-state drives, USB flash drives, micro-SD cards, or other types of removable memory, and/or other types and kinds of memory.

The communication interfaces 710B/710C can be local area network (LAN), wide area network (WAN), universal serial bus (USB), Ethernet, RS232, RS485, serial, Wi-Fi, 802.11abgn and similar, 2G 3G 4G 5G compatible, Bluetooth, transmission control protocol (TCP), user datagram protocol (UDP), Mesh Network, Zigbee, Pico Network, long-range navigation (LORAN), and/or other types and kinds of communication interfaces and protocols.

Display 712B/712C can be a liquid crystal display (LCD), light emitting diode (LED), organic light emitting diode (OLED), or other types and kinds of displays.

The general-purpose inputs and outputs (GPIO) 714B/714C can be TTL, CMOS, MOSFET, transistors, buffers, relays, pushbuttons, switches, and/or other types and kinds of GPIO circuits. In an exemplary embodiment, some of the GPIO 214 lines can be used to drive a touch screen input, biometric input devices, keyboards, and/or types and kinds of computing device input devices.

Global positioning system (GPS) device 716 can be used to determine the geographic location of technician 302 and others who are carrying a computing device 732 equipped with a GPS 716. In this regard, such computing devices 732 are typically mobile computing devices such as tablets 732A, smartphones 732B, and other similar types and/or kinds of mobile computing devices 732.

Microphone and/or camera 718 can be used to record audio, and video, and take pictures. In this regard, users 304/306 can use their computing devices equipped with a microphone and/or camera 718 to make digital media records that can be selectively shared as appropriate including on social media and other digital media outlet locations.

With reference to FIG. 6, the data processing resource 702 can be a server, network storage device, or other types and kinds of data processing resources. Such data processing resources can be AMAZON WEB SERVICES (AWS), MICROSOFT AZURE, or other types and kinds of hosted data processing resource services. For disclosure purposes, a remote data processing resource 702 can also be referred to as server 702.

The data processing resource 702 can comprise a microprocessor 704A, a database 706A, memory 708A, and a communication interface 710A. The microprocessor 704A is operationally related to database 706A, memory 708A, and communication interface 710A.

The microprocessor 704A can be INTEL, ZILOG, MICROCHIP, AMD, ARM, and/or other types or kinds of microprocessors.

The database 706A can be SQL, MYSQL, MARIADB, ORACLE, MS ACCESS, network accessible storage, flat files, a combination thereof, or other types and kinds of databases.

The memory 708A can be a combination of RAM, ROM, flash, hard drives, solid-state drives, USB flash drives, micro-SD cards, or other types of removable memory, and/or other types and kinds of memory.

The communication interfaces 710A can be LAN, WAN, USB, Ethernet, RS232, RS485, serial, Wi-Fi, 802.11abgn and similar, 2G 3G 4G 5G compatible, Bluetooth, TCP, UDP, Mesh Network, Zigbee, Pico Network, LORAN, and/or other types and kinds of communication interfaces and protocols.

Figure 7:
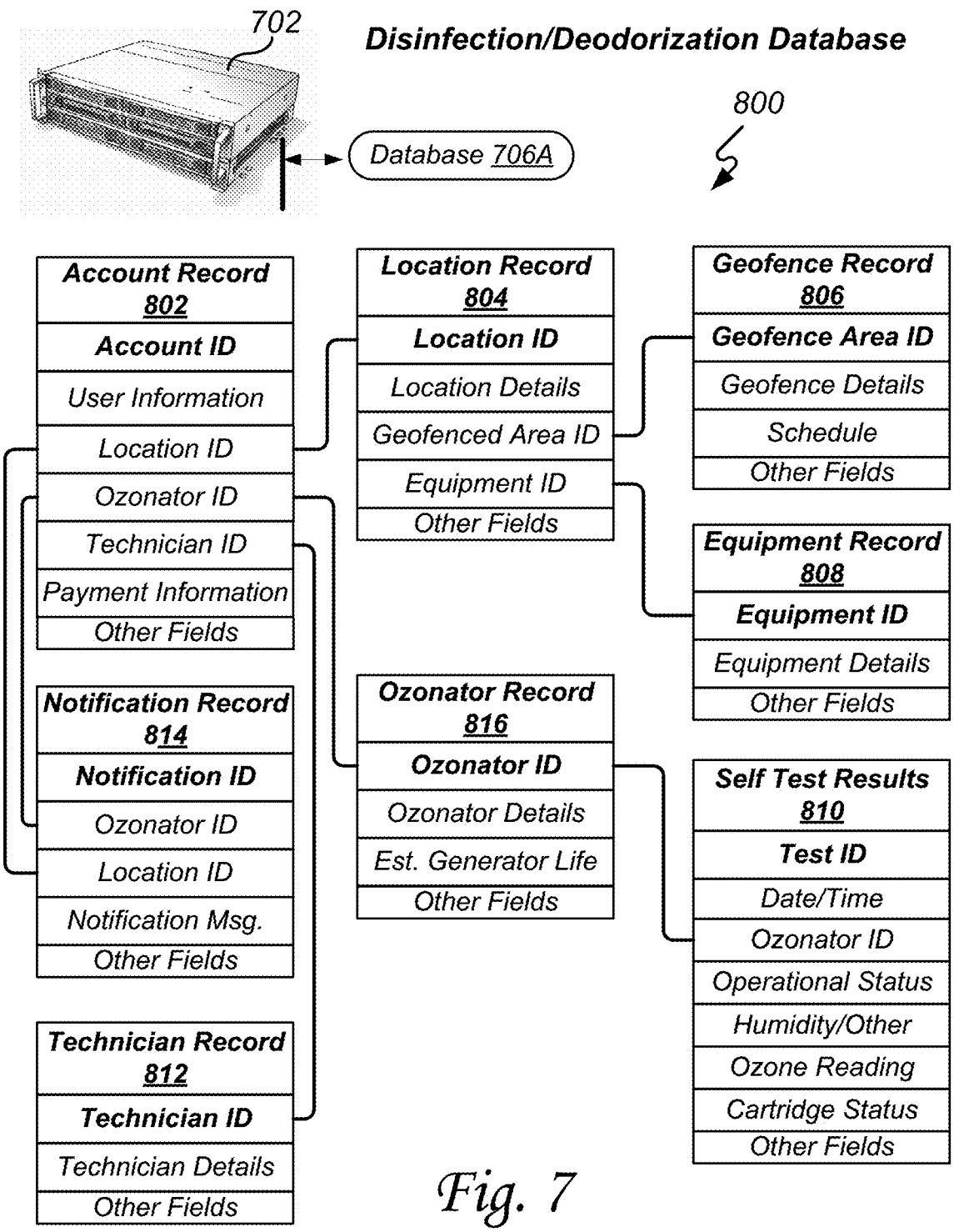
FIG. 7 illustrates one example of an ozone disinfection database structure.

Referring to FIG. 7, there is illustrated one example of an ozone disinfection/deodorization database structure 800. In an exemplary embodiment, at least one database 706A/706B/706C can be implemented on at least one of the data processing resources 702 also referred to as server 702, or computing devices 732. In operation, one or more databases 706A/706B/706C can be accessed/created/managed/maintained as appropriate by more than one stakeholder. In this regard, in addition to system administrators and other authorized persons, other stakeholders can access/create/manage/maintain as appropriate.

In an exemplary embodiment, such databases 706A/706B/706C can be SQL, MYSQL, MARIADB, ORACLE, MS ACCESS, network-accessible storage, flat files, a combination thereof, or other types and kinds of databases.

In an exemplary embodiment, the ozone disinfection/deodorization database 900 can reside on a remote data processing resource 702 in database 706A. In this regard, the ozone disinfection/deodorization database 900 can comprise a series of tables, records, fields, and accounts that include account record 802, location record 804, geofence record 806, equipment record 808, self-test results 810, technician record 812, notification record 814, ozonator record 816, and/or other types or kinds of records as may be required and/or desired in a particular embodiment. The database structure illustrated in FIG. 7 also illustrates the relationship between the various tables.

In an exemplary embodiment, the data structure is illustrative and can be expanded and modified without particular limitation as needed and as appropriate to support the functionality and methods of the present invention and to support future functionality and methods of the present invention as it grows and evolves over time.

Figure 8:
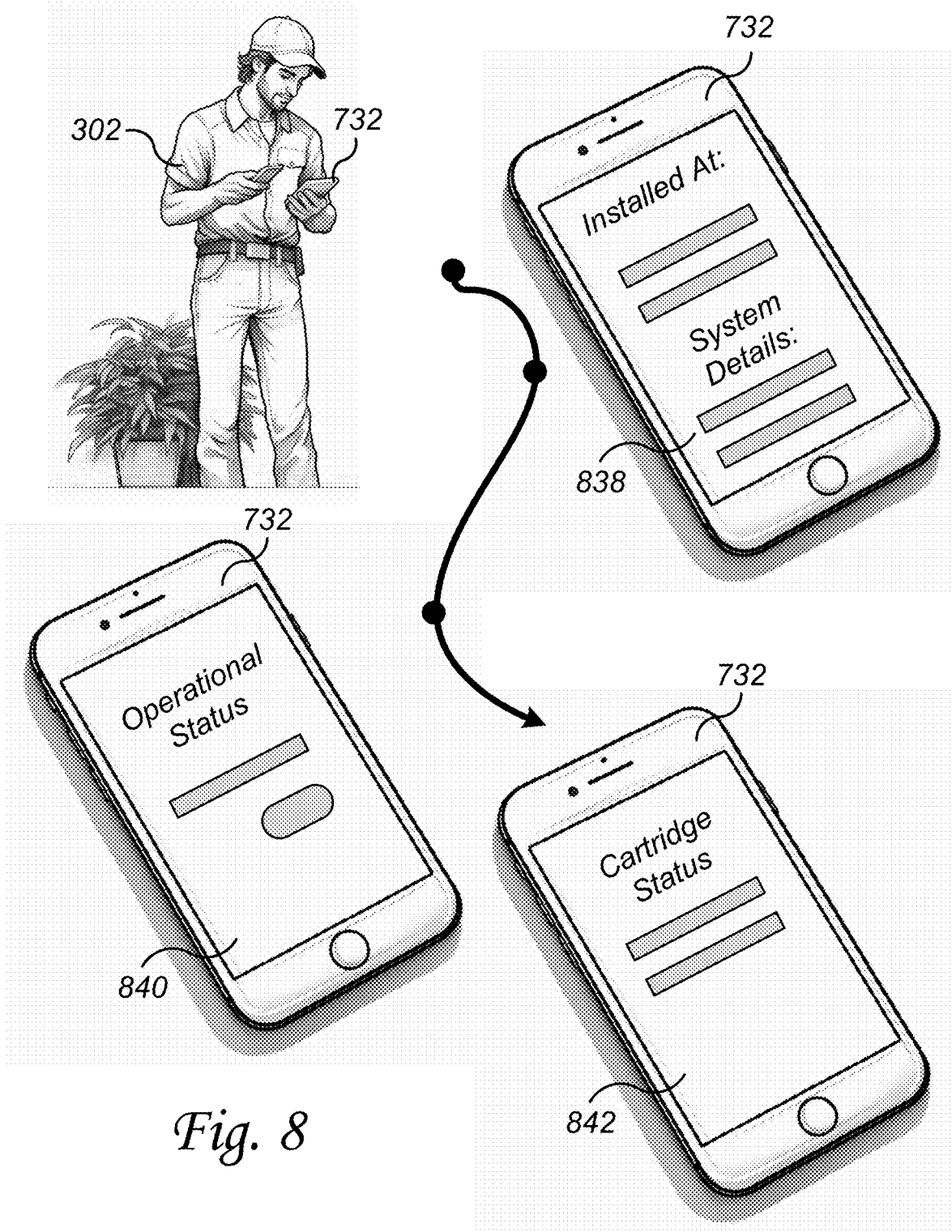
FIG. 8 illustrates one example of a technician's use of a software application.

Referring to FIG. 8, a technician's use of a software application. In an exemplary embodiment, a software application or website can be used in combination with the computing device 732A/B to identify the aqueous ozone air deodorizing system 100, view operational statuses, record the test results and other results, and see other useful data by way of data communicating with a remote data processing resource 702. In some embodiments, certain air deodorizing system 100 may have the ability to data communicate 734 directly with a remote data processing resource 702, eliminating the need for computing device 732A/B to act as an intermediary device to record test results on the remote data processing resource 702.

In an exemplary embodiment and with reference to at least FIG. 8, a computing device 732, operated by technician 302, data communicates with a remote data processing resource 702, and receives from the remote data processing resource 702, by way of the computing device 732 a plurality of air deodorizing system 100 location 838 and service life data 840/742 that corresponds to the remaining service life the electrochemical generator 516, the plurality of titanium oxide particles 110, the plurality of manganese dioxide particles 112, and other service life information, as may be required and/or desired in a particular embodiment.

Figure 9:
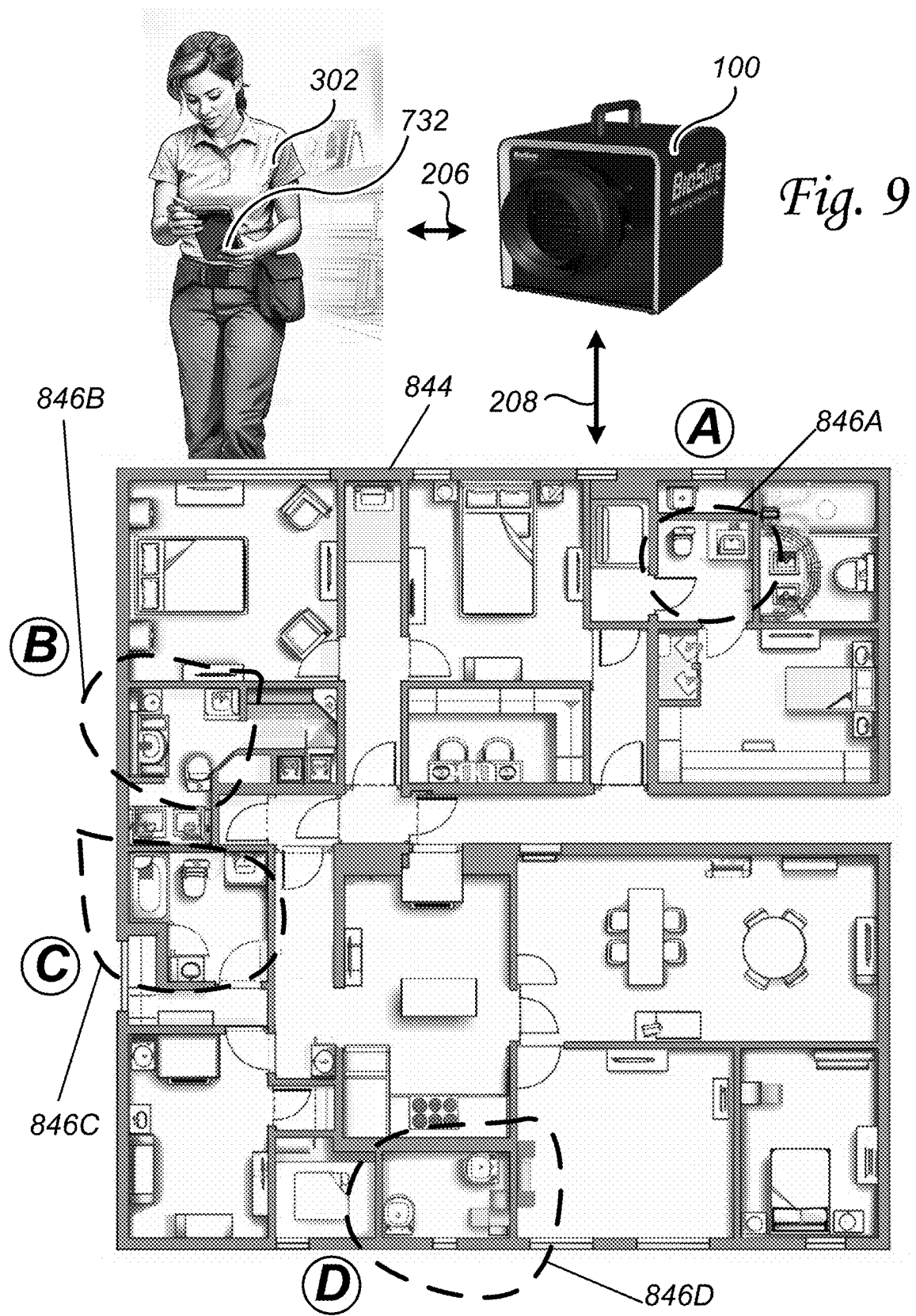
FIG. 9 illustrates one example of a floor plan to monitor geofenced or geolocate room spaces that have installed an air deodorizing system.

Referring to FIG. 9, there is illustrated one example of a floor plan 844 to monitor geofenced or geolocate room spaces 'A' 846A, 'B' 846B, 'C' 846C, and 'D' 846D that have installed 208 an air deodorizing system 100. In an exemplary embodiment, technician 302, by way of computing platform 732, can data communicate with server 732 or data communicate 206 with individual air deodorizing system 100 to ascertain operational status and location with a floor plan area 844.

Figure 10:
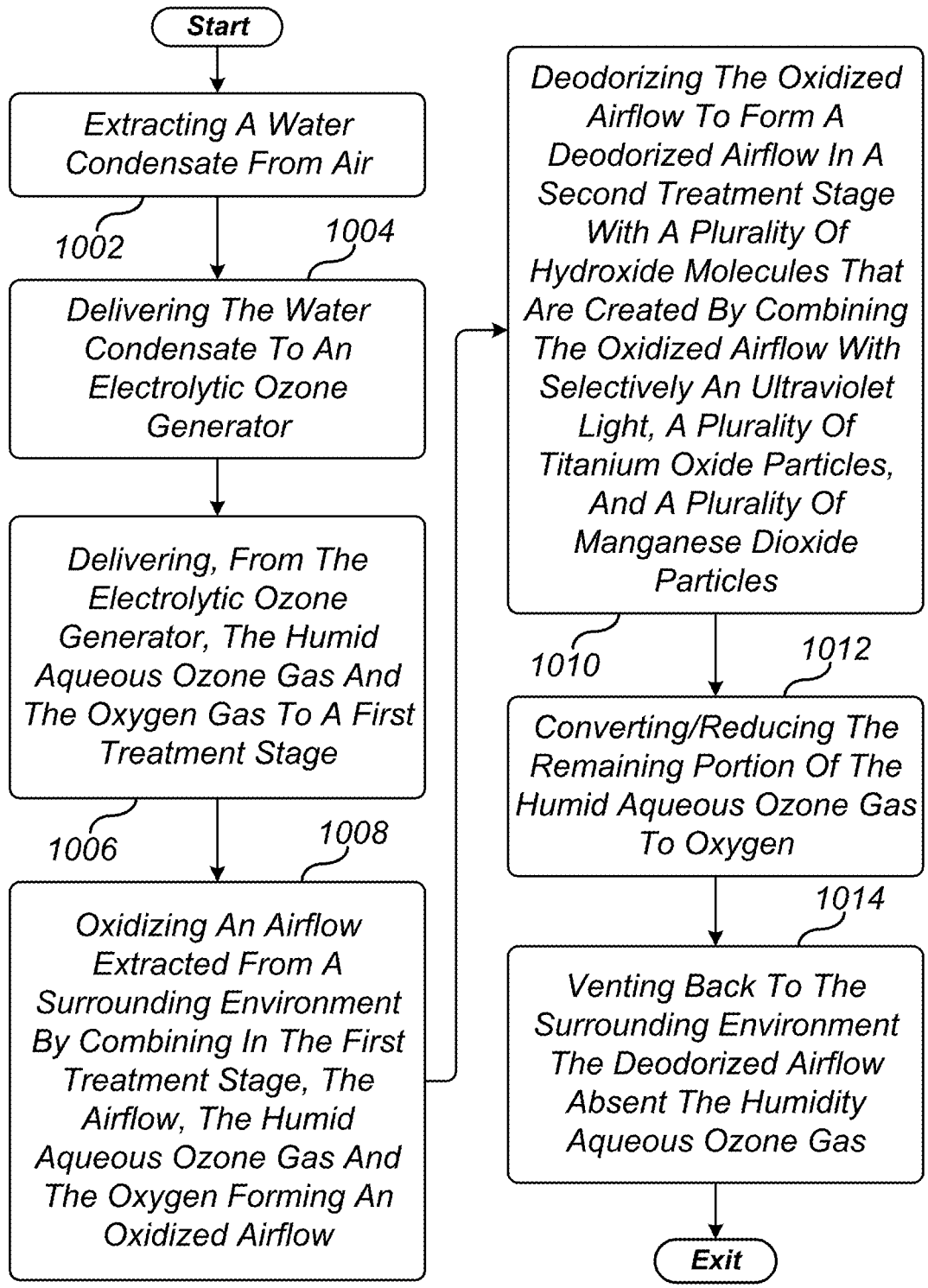
FIGS. 10-13 illustrates examples of methods of deodorizing air using aqueous ozone as a catalyst.

Referring to FIG. 10, there is illustrated one example of a method of deodorizing air using aqueous ozone as a catalyst. In an exemplary embodiment, a method of deodorizing air using aqueous ozone as a catalyst begins in step 1002 by extracting a water condensate 204 from the air in a surrounding environment and then in step 1004 by delivering the water condensate 204 to an electrochemical ozone generator 516 to form a humid aqueous ozone gas, an oxygen gas, and selectively a hydrogen gas. In this regard, delivery can include pumping 128, piping or tube 136, check valves 130, or other suitable solutions to transfer the condensate water 204 from tank 126 or otherwise to the electrochemical ozone generator 516.

The method continues in step 1006 by delivering, from the electrochemical ozone generator 516, the humid aqueous ozone gas and the oxygen gas to a first treatment stage 410. In this regard, delivering can include pumping, piping/tubing 120, or other suitable solutions to transfer the humid aqueous ozone gas, the oxygen gas, and the hydrogen gas to a first treatment stage 410.

The method continues in step 1008 by oxidizing an airflow 402 extracted from a surrounding environment 202 by combining, in the first treatment stage 410, the airflow 402 with the humid aqueous ozone gas and the oxygen forming an oxidized airflow 404.

The method continues in step 1010 by deodorizing the oxidized airflow 404 to form a deodorized airflow 406 in a second treatment stage 412 with a plurality of hydroxide molecules that are created by combining the oxidized airflow 404 with ultraviolet light 108, a plurality of titanium oxide particles 110, and a plurality of manganese dioxide particles 112. In an exemplary embodiment, the plurality of manganese dioxide particles can be a plurality of sintered columnar manganese dioxide particles or other suitable manganese dioxide.

The method continues in step 1012 by converting the remaining portion of the humid aqueous ozone gas within the deodorized airflow 406 to oxygen by way of interaction with the plurality of titanium oxide particles 110 and the plurality of manganese dioxide particles 112.

The method continues in step 1014 venting 408 back to the surrounding environment 202 the deodorized airflow 406 with the humid aqueous ozone gas at or below a human-safe permissible level. The method is then exited.

Figure 11:
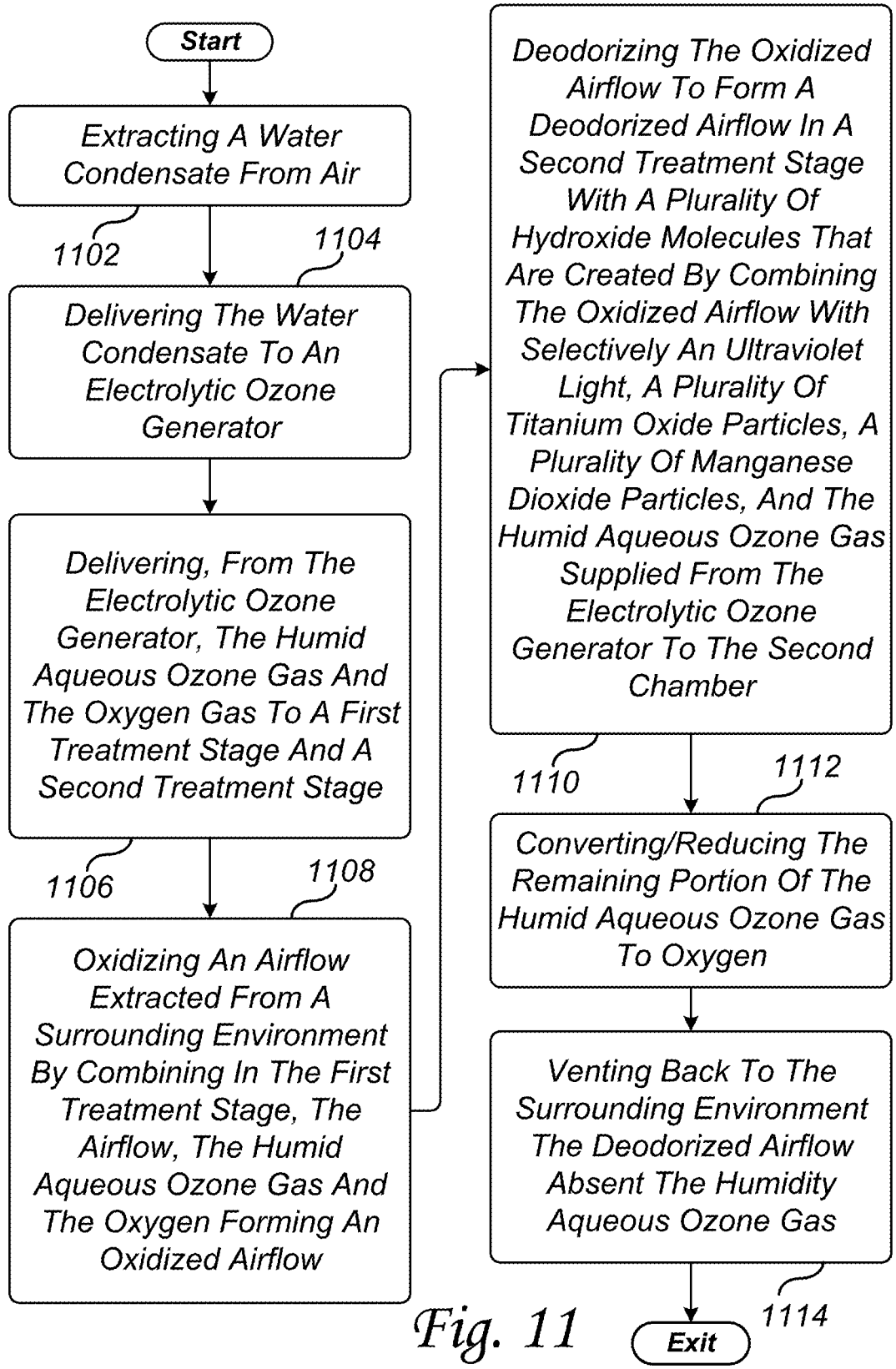

Referring to FIG. 11, there is illustrated one example of a method of deodorizing air using aqueous ozone as a catalyst. In an exemplary embodiment, a method begins in step 1102 by extracting a water condensate 204 from air 204 in a surrounding environment and in step 1104 by delivering the water condensate 204 to an electrochemical ozone generator 516 to form a humid aqueous ozone gas, an oxygen gas, and selectively a hydrogen gas. In this regard, delivery can include pumping 128, piping or tube 136, check valves 130, or other suitable solutions to transfer the condensate water 204 from tank 126 or otherwise to the electrochemical ozone generator 516.

The method continues in step 1106 by delivering, from the electrochemical ozone generator 516, the humid aqueous ozone gas and the oxygen gas, and the hydrogen gas to a first treatment stage 410 and a second treatment stage 412. In this regard, delivering can include pumping, piping or tubes 120/122, interconnection with and use of inlet 114, or other suitable solutions to transfer the humid aqueous ozone gas, the oxygen gas, and the hydrogen gas to a first treatment stage 410 and the second treatment stage 412.

The method continues in step 1108 by oxidizing an airflow 402 extracted from a surrounding environment 202 by combining, in the first treatment stage 410, the airflow 402 with the humid aqueous ozone gas, the oxygen, and the hydrogen forming an oxidized airflow 404.

The method continues in step 1110 by deodorizing the oxidized airflow 404 to form a deodorized airflow 406 in a second treatment stage 412 with a plurality of hydroxide molecules that are created by combining the oxidized airflow 404 with ultraviolet light 108, a plurality of titanium oxide particles 110, a plurality of manganese dioxide particles 112, and the humid aqueous ozone gas supplied from the electrochemical ozone generator 516 to the second treatment stage 412. In an exemplary embodiment, the plurality of manganese dioxide particles can be a plurality of sintered columnar manganese dioxide particles or other suitable manganese dioxide.

The method continues in step 1112 by converting the remaining portion of the humid aqueous ozone gas within the deodorized airflow 406 to oxygen by way of interaction with the plurality of titanium oxide particles 110, and the plurality of manganese dioxide particles 112.

The method continues in step 1114 by venting 408 back to the surrounding environment 202 the deodorized airflow 406 with the humid aqueous ozone gas at or below a human-safe permissible level. The method is then exited.

Figure 12:
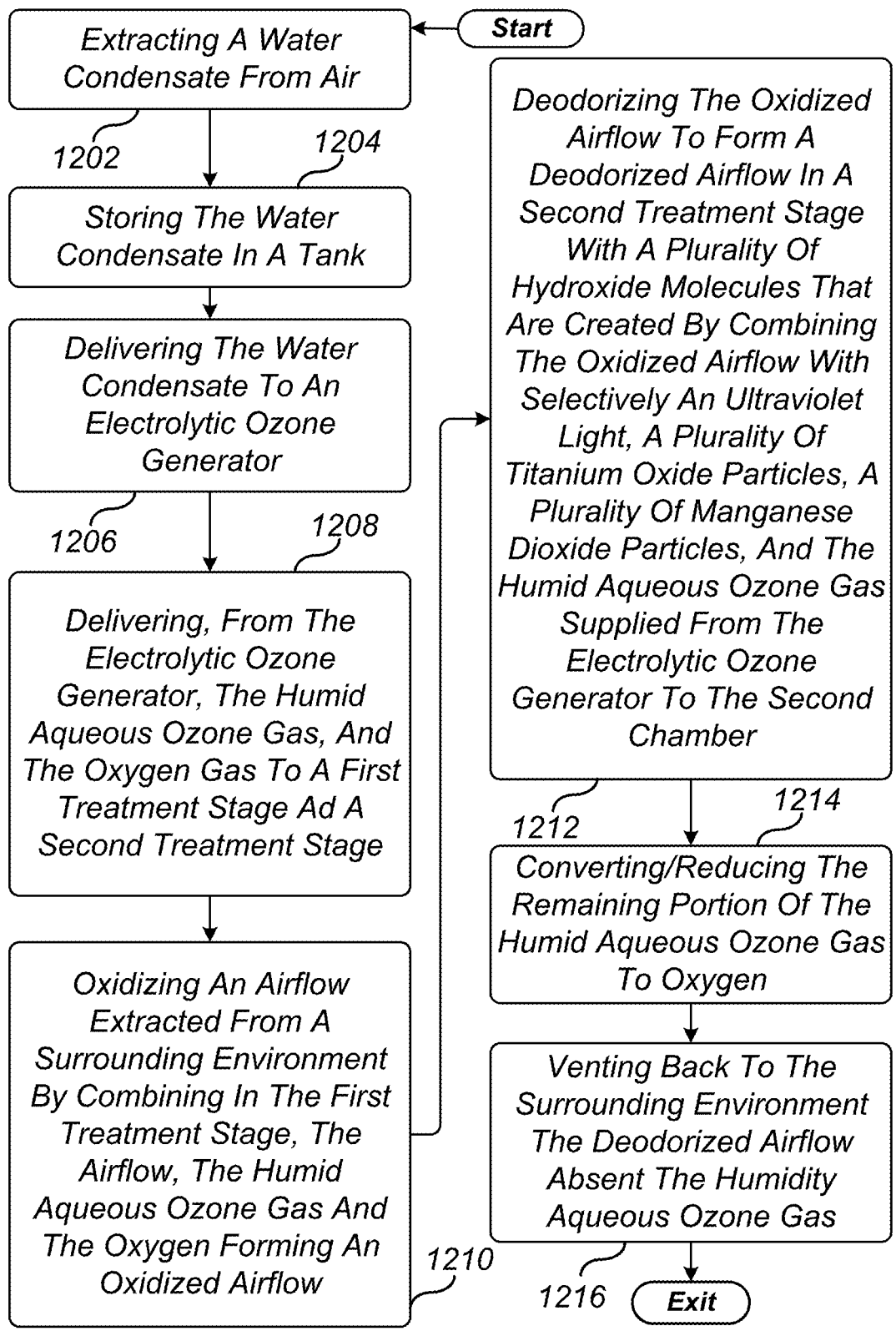

Referring to FIG. 12, there is illustrated one example of a method of deodorizing air using aqueous ozone as a catalyst. In an exemplary embodiment, a method of deodorizing air using aqueous ozone as a catalyst begins in step 1202 by extracting a water condensate 204 from air in a surrounding environment, then in step 1204 by storing the water condensate 204 in a tank 126, and in step 1206 by delivering, from the tank, the water condensate to an electrochemical ozone generator to form a humid aqueous ozone gas, an oxygen gas, and a hydrogen gas. In this regard, delivery can include pumping 128, piping or tube 136, check valves 130, or other suitable solutions to transfer the condensate water 204 from tank 126 or otherwise to the electrochemical ozone generator 516.

The method continues in step 1208 by delivering, from the electrochemical ozone generator 516, the humid aqueous ozone gas, the oxygen gas, and the hydrogen gas to a first treatment 410. In this regard, delivering can include pumping, piping or tube 120, or other suitable solutions to transfer the humid aqueous ozone gas, the oxygen gas, and the hydrogen gas to a first treatment stage 410.

The method continues in step 1210 by oxidizing an airflow 402 extracted from a surrounding environment 202 by combining, in the first treatment stage 410, the airflow 402 with the humid aqueous ozone gas, the oxygen, and the hydrogen forming an oxidized airflow.

The method continues in step 1212 by deodorizing the oxidized airflow 404 to form a deodorized airflow 406 in a second treatment stage 412 with a plurality of hydroxide molecules that are created by combining the oxidized airflow 404 with ultraviolet light 108, a plurality of titanium oxide particles 110, a plurality of manganese dioxide particles 112, and the humid aqueous ozone gas supplied from the electrochemical ozone generator 516 to the second treatment stage 412.

The method continues in step 1214 by converting the remaining portion of the humid aqueous ozone gas within the deodorized airflow 406 to oxygen by way of interaction with the plurality of titanium oxide particles 110, and the plurality of manganese dioxide particles 112. In an exemplary embodiment, the plurality of manganese dioxide particles can be a plurality of sintered columnar manganese dioxide particles or other suitable manganese dioxide.

The method continues in step 1216 by venting 408 back to the surrounding environment 202 the deodorized airflow 406 with the humid aqueous ozone gas at or below a human-safe permissible level.

Figure 13:
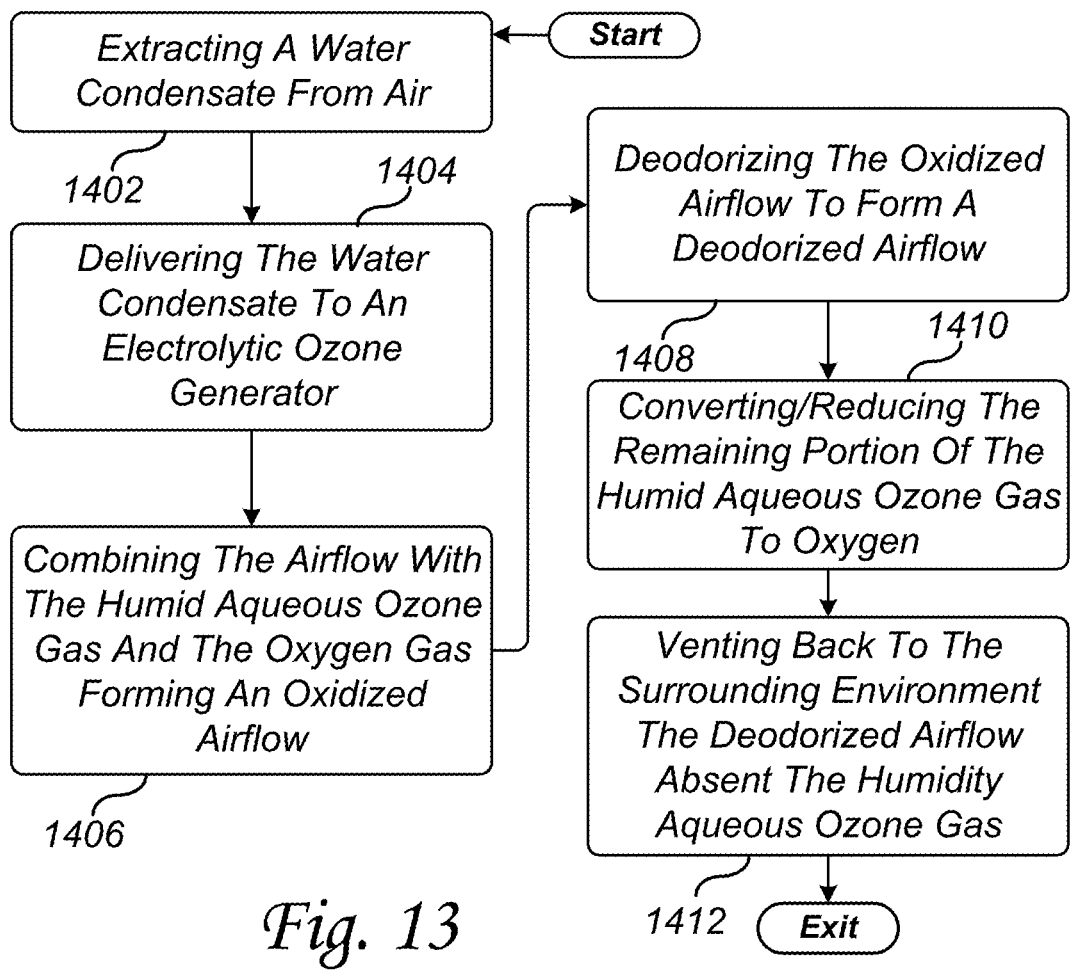

Referring to FIG. 13, there is illustrated one example of a method of deodorizing air using aqueous ozone as a catalyst. In an exemplary embodiment, a method of deodorizing air using aqueous ozone as a catalyst begins in step 1402 by extracting water condensate 204 from the air in a surrounding environment.

The method continues in step 1404 by delivering the water condensate 204 to an electrochemical ozone generator 516 to form a humid aqueous ozone gas and an oxygen gas.

The method continues in step 1406 by combining the airflow 402 with the humid aqueous ozone gas and the oxygen gas forming an oxidized airflow 404.

The method continues in step 1408 by deodorizing the oxidized airflow to form a deodorized airflow 406 with a plurality of hydroxide molecules that are created by combining the oxidized airflow 404 with a plurality of titanium oxide particles 110 and a plurality of manganese dioxide particles 112.

The method continues in step 1410 by converting the remaining portion of the humid aqueous ozone gas within the deodorized airflow 406 to oxygen by way of interaction with the plurality of titanium oxide particles 110 and the plurality of manganese dioxide particles 112.

The method continues in step 1412 by venting the deodorized airflow back to the surrounding environment with the humid aqueous ozone gas at or below a human-safe permissible level.

Figure 14:
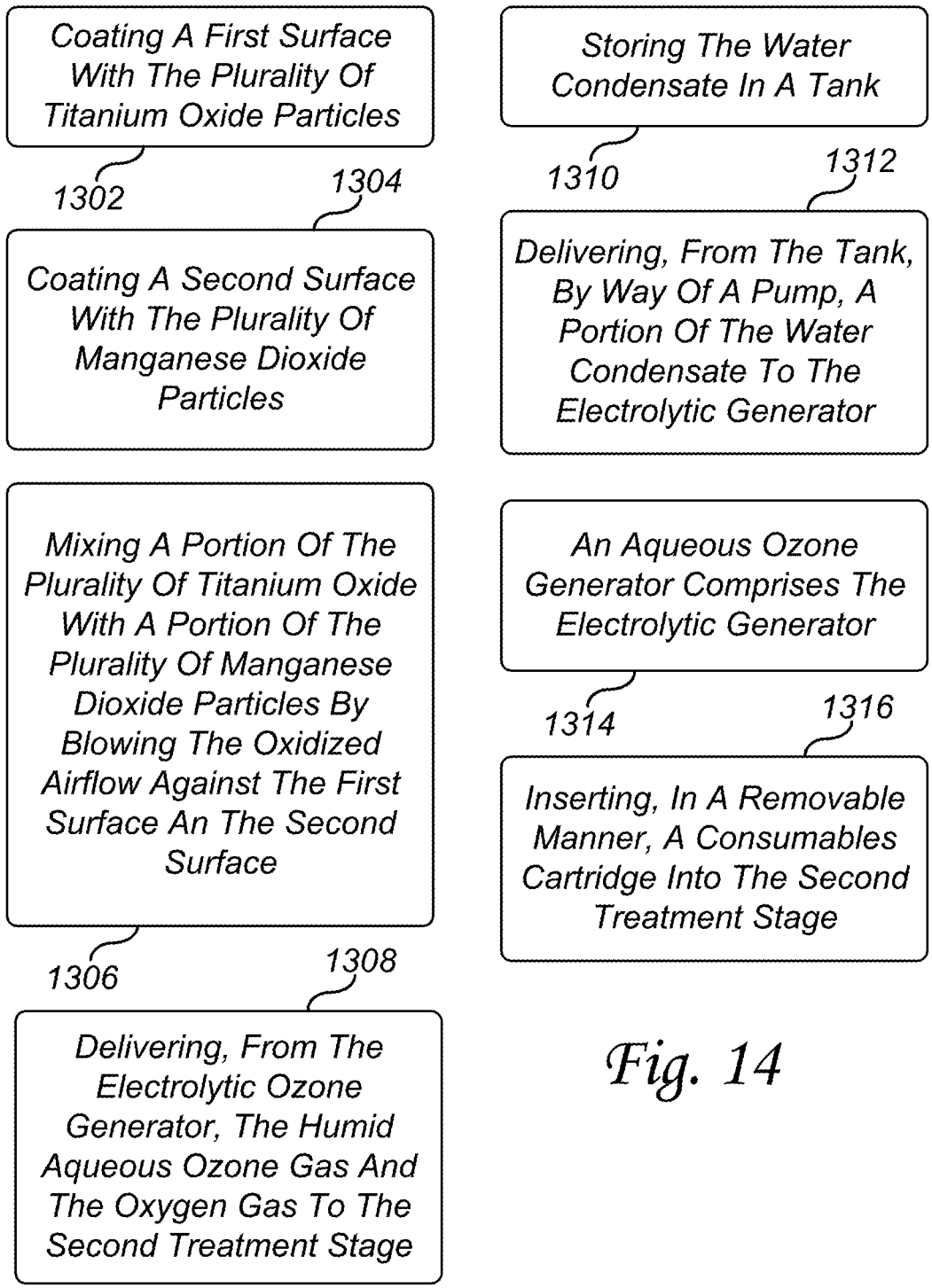
FIGS. 14-15 illustrate exemplary embodiments that can be used interchangeably with the methods of the present invention.

Referring to FIG. 14, there are illustrated exemplary embodiments that can be used interchangeably with the methods of the present invention.

In step 1302, by coating a first surface 138 with the plurality of titanium oxide particles 110.

In step 1304, by coating a second surface 140 with the plurality of sintered columnar manganese dioxide particles 112.

In step 1306, by mixing a portion of the plurality of titanium oxide particles 110 with a portion of the plurality of sintered columnar manganese dioxide particles 112 by blowing the oxidized airflow 404 against the first surface 138 and the second surface 140.

In step 1308, delivering, from the electrochemical ozone generator 516, the humid aqueous ozone gas, the oxygen gas, and the hydrogen gas to the second treatment stage 412.

In step 1310, by storing the water condensate 204 in tank 126.

In step 1312, by delivering, from tank 126, by way of pump 128, a portion of the water condensate 204 to an electrochemical ozone generator 516.

In step 1314, an aqueous ozone generator 530 can comprise the electrochemical ozone generator 516.

In step 1316 by inserting 414, in a removable manner, a consumables cartridge 116 into the second treatment stage 412. The consumables cartridge 116 can comprise the plurality of titanium oxide particles 410 and the plurality of sintered columnar manganese dioxide particles 412.

Figure 15:
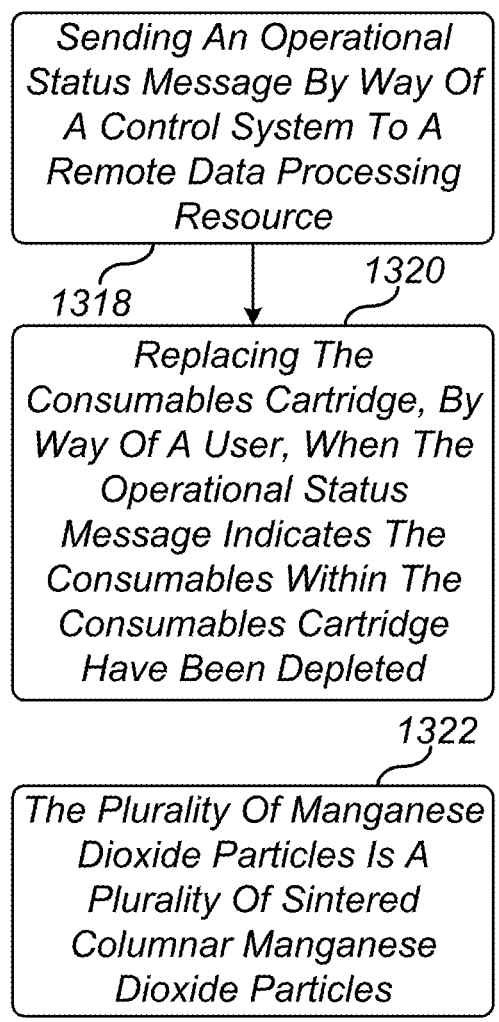

Referring to FIG. 15, there are illustrated exemplary embodiments that can be used interchangeably with the methods of the present invention.

In step 1318, sending an operational status message by way of a control system 500 to a remote data processing resource 702. The method then moves to step 1320.

In step 1320, replacing the consumables cartridge 116, by way of user 302, when the operational status message indicates the consumables within the consumables cartridge 116 have been depleted.

In step 1322, in an exemplary embodiment, the plurality of manganese dioxide particles can be a plurality of sintered columnar manganese dioxide particles or other suitable manganese dioxide.

The capabilities of the present invention can be implemented in software, firmware, hardware, or some combination thereof.

As one example, one or more aspects of the present invention can be included in an article of manufacture (e.g., one or more computer program products) having, for instance, computer-usable media. The media has embodied therein, for instance, computer-readable program code means for providing and facilitating the capabilities of the present invention. The article of manufacture can be included as a part of a computer system or sold separately.

Additionally, at least one program storage device readable by a machine, tangibly embodying at least one program of instructions executable by the machine to perform the capabilities of the present invention can be provided.

The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

While the preferred embodiment of the invention has been described, it will be understood that those skilled in the art, both now and in the future, may make various improvements and enhancements which fall within the scope of the claims which follow. These claims should be construed to maintain the proper protection for the invention first described.

What is claimed is:

1. A method of deodorizing air comprising the steps of:
    delivering water to an electrochemical ozone generator to form an aqueous ozone gas and an oxygen gas;
    delivering, from the electrochemical ozone generator, the aqueous ozone gas and the oxygen gas to a first treatment stage;

oxidizing an airflow extracted from a surrounding environment by combining, in the first treatment stage, the airflow with the aqueous ozone gas and the oxygen gas forming an oxidized airflow;

deodorizing the oxidized airflow to form a deodorized airflow in a second treatment stage with a plurality of hydroxide molecules that are created by combining the oxidized airflow with an ultraviolet light, a plurality of titanium oxide particles, and a plurality of manganese dioxide particles;

reducing to a human-safe permissible level the remaining portion of the aqueous ozone gas in the deodorized airflow to oxygen by way of an interaction with the plurality of titanium oxide particles and the plurality of manganese dioxide particles; and venting the deodorized airflow back into the surrounding environment with the aqueous ozone gas level at or below the human-safe permissible level.

2. The method in accordance with claim 1, wherein range of the human-safe permissible level is less than 0.1 parts-per-million (ppm) for an 8-hour workday and a 40-hour work week.

3. The method in accordance with claim 1, wherein the plurality of manganese dioxide particles is a plurality of sintered columnar manganese dioxide particles.

4. The method in accordance with claim 1, further comprising the step of:
coating a first surface with the plurality of titanium oxide particles.

5. The method in accordance with claim 4, further comprising the step of:
coating a second surface with the plurality of manganese dioxide particles.

6. The method in accordance with claim 5, further comprising the step of:
mixing a portion of the plurality of titanium oxide particles with a portion of the plurality of manganese dioxide particles by blowing the oxidized airflow against the first surface and the second surface.

7. The method in accordance with claim 1, further comprising the step of:
delivering, from the electrochemical ozone generator, the aqueous ozone gas and the oxygen gas to the second treatment stage.

8. The method in accordance with claim 1, further comprising the step of:
storing water used for the electrochemical ozone generator in a tank.

9. The method in accordance with claim 8, the step of delivering the water condensate to the electrochemical ozone generator further comprises:
delivering, from the tank, by way of a pump, a portion of the water condensate to an electrochemical ozone generator.

10. The method in accordance with claim 1, an aqueous ozone generator comprises the electrochemical ozone generator.

11. The method in accordance with claim 1, further comprising the step of:
inserting, in a removable manner, a consumables cartridge which comprises the plurality of titanium oxide particles and the plurality of manganese dioxide particles.

12. The method in accordance with claim 11, further comprising the steps of:
sending an operational status message by way of a control system to a remote data processing resource; and replacing the consumables cartridge, by way of a user, when the operational status message indicates the consumables within the consumables cartridge have been depleted.

13. A method of deodorizing air comprising the steps of:
extracting a water condensate from air in a surrounding environment;

delivering the water condensate to an electrochemical ozone generator to form a humid aqueous ozone gas and an oxygen gas;

combining an airflow with the humid aqueous ozone gas and the oxygen gas forming an oxidized airflow;

deodorizing the oxidized airflow to form a deodorized airflow with a plurality of hydroxide molecules that are created by combining the oxidized airflow with a plurality of titanium oxide particles and a plurality of manganese dioxide particles;

reducing to a human-safe permissible level the remaining portion of the humid aqueous ozone gas in the deodorized airflow to oxygen by way of an interaction with the plurality of titanium oxide particles and the plurality of manganese dioxide particles; and venting the deodorized airflow back into the surrounding environment with the humid aqueous ozone gas level at or below the human-safe permissible level.

14. The method in accordance with claim 13, the step of deodorizing the oxidized airflow further comprising:
combining the oxidized airflow with an ultraviolet light, the plurality of titanium oxide particles and the plurality of manganese dioxide particles.

15. The method in accordance with claim 13, wherein the plurality of manganese dioxide particles is a plurality of sintered columnar manganese dioxide particles.

16. The method in accordance with claim 13, further comprising the step of:
mixing, by blowing the oxidized airflow against, the plurality of titanium oxide particles with the plurality of manganese dioxide particles.

17. The method in accordance with claim 13, an aqueous ozone generator comprises the electrochemical ozone generator.

18. The method in accordance with claim 13, further comprising the step of:
inserting, in a removable manner, a consumables cartridge which comprises the plurality of titanium oxide particles and the plurality of manganese dioxide particles.

19. The method in accordance with claim 18, further comprising the steps of:
sending an operational status message by way of a control system to a remote data processing resource; and replacing the consumables cartridge, by way of a user, when the operational status message indicates the consumables within the consumables cartridge have been depleted.

20. A method of deodorizing air comprising the steps of:
extracting a water condensate from air in a surrounding environment;

delivering the water condensate to an electrochemical ozone generator to form a humid aqueous ozone gas and an oxygen gas;

combining an airflow with the humid aqueous ozone gas and the oxygen gas forming an oxidized airflow;

deodorizing the oxidized airflow to form a deodorized airflow with a plurality of hydroxide molecules that are created by combining the oxidized airflow with an ultraviolet light and a plurality of titanium oxide particles;

reducing to a human-safe permissible level the remaining portion of the humid aqueous ozone gas in the deodorized airflow to oxygen by way of an interaction with the plurality of titanium oxide particles and a plurality of manganese dioxide particles; and venting the deodorized airflow back into the surrounding environment with the humid aqueous ozone gas level at or below the human-safe permissible level.

21. The method in accordance with claim 20, the step of deodorizing the oxidized airflow further comprising:

combining the oxidized airflow with the ultraviolet light, the plurality of titanium oxide particles, and the plurality of manganese dioxide particles.

22. The method in accordance with claim 20, wherein the plurality of manganese dioxide particles is a plurality of sintered columnar manganese dioxide particles.

23. The method in accordance with claim 20, further comprising the step of:

mixing, by blowing the oxidized airflow against, the plurality of titanium oxide particles with the plurality of manganese dioxide particles.

24. The method in accordance with claim 20, further comprising the step of:

inserting, in a removable manner, a consumables cartridge which comprises the plurality of titanium oxide particles and the plurality of manganese dioxide particles.

25. The method in accordance with claim 24, further comprising the steps of:

sending an operational status message by way of a control system to a remote data processing resource; and replacing the consumables cartridge, by way of a user, when the operational status message indicates the consumables within the consumables cartridge have been depleted.

* * * * *